(12) United States Patent  (10) Patent No.: US 8,048,998 B2
Rasmussen et al.  (45) Date of Patent: Nov. 1, 2011

(54) MEDIATED CELLULAR DELIVERY OF LNA OLIGONUCLEOTIDES

(75) Inventors: Soeren Vestergaard Rasmussen, Nivaa (DK); Torsten Bryld, Copenhagen S (DK); Soeren Moeller, Holte (DK)

(73) Assignee: Exiqon A/S, Vedbaek (DK)

( * ) Notice: Subject to any disclaimer, the term of this patent is extended or adjusted under 35 U.S.C. 154(b) by 0 days.

(21) Appl. No.: 12/523,678

(22) PCT Filed: Jan. 18, 2008

(86) PCT No.: PCT/DK2008/000019
§ 371 (c)(1), (2), (4) Date: Sep. 15, 2009

(87) PCT Pub. No.: WO2008/086807
PCT Pub. Date: Jul. 24, 2008

(65) Prior Publication Data
US 2010/0035968 A1  Feb. 11, 2010

(30) Foreign Application Priority Data
Jan. 19, 2007 (DK) ................................ 2007 00087

(51) Int. Cl.
C07H 21/04 (2006.01)
A61K 31/70 (2006.01)
(52) U.S. Cl. ......................................... 536/23.1; 514/44
(58) Field of Classification Search .................. None
See application file for complete search history.

(56) References Cited

U.S. PATENT DOCUMENTS

| | | | |
|---|---|---|---|
| 3,687,808 A | 8/1972 | Merigan, Jr. et al. | |
| 4,426,330 A | 1/1984 | Sears | |
| 4,534,899 A | 8/1985 | Sears | |
| 4,837,028 A | 6/1989 | Allen | |
| 5,013,556 A | 5/1991 | Woodle et al. | |
| 5,108,921 A | 4/1992 | Low et al. | |
| 5,213,804 A | 5/1993 | Martin et al. | |
| 5,225,212 A | 7/1993 | Martin et al. | |
| 5,227,170 A | 7/1993 | Sullivan | |
| 5,264,221 A | 11/1993 | Tagawa et al. | |
| 5,354,844 A | 10/1994 | Beug et al. | |
| 5,356,633 A | 10/1994 | Woodle et al. | |
| 5,395,619 A | 3/1995 | Zalipsky et al. | |
| 5,416,016 A | 5/1995 | Low et al. | |
| 5,417,978 A | 5/1995 | Tari et al. | |
| 5,432,272 A | 7/1995 | Benner | |
| 5,459,127 A | 10/1995 | Felgner et al. | |
| 5,469,854 A | 11/1995 | Unger et al. | |
| 5,512,295 A | 4/1996 | Kornberg et al. | |
| 5,521,291 A | 5/1996 | Curiel et al. | |
| 5,527,528 A | 6/1996 | Allen et al. | |
| 5,534,259 A | 7/1996 | Zalipsky et al. | |
| 5,540,935 A | 7/1996 | Miyazaki et al. | |
| 5,543,152 A | 8/1996 | Webb et al. | |
| 5,543,158 A | 8/1996 | Gref et al. | |
| 5,547,932 A | 8/1996 | Curiel et al. | |
| 5,556,948 A | 9/1996 | Tagawa et al. | |
| 5,580,575 A | 12/1996 | Unger et al. | |
| 5,583,020 A | 12/1996 | Sullivan | |
| 5,591,721 A | 1/1997 | Agrawal et al. | |
| 5,595,756 A | 1/1997 | Bally et al. | |
| 5,665,710 A | 9/1997 | Rahman et al. | |
| 5,705,188 A | 1/1998 | Junichi et al. | |
| 5,770,713 A | 6/1998 | Imbach et al. | |
| 6,043,060 A | 3/2000 | Imanishi | |
| 6,268,490 B1 | 7/2001 | Imanishi et al. | |
| 6,670,461 B1 | 12/2003 | Nielsen et al. | |
| 6,794,499 B2 | 9/2004 | Wengel et al. | |
| 6,887,906 B1 | 5/2005 | Teng et al. | |
| 2002/0068709 A1* | 6/2002 | Orum et al. ..................... | 514/44 |
| 2002/0177150 A1* | 11/2002 | Manoharan et al. .............. | 435/6 |
| 2006/0094045 A1* | 5/2006 | Chang et al. ...................... | 435/6 |

FOREIGN PATENT DOCUMENTS

| | | |
|---|---|---|
| EP | 0 445 131 | 9/1991 |
| EP | 0 496 813 | 8/1992 |
| EP | 1 072 679 | 1/2001 |
| WO | WO 88/04924 | 7/1988 |
| WO | WO 90/04384 | 5/1990 |
| WO | WO 91/05545 | 5/1991 |
| WO | WO 93/24510 | 12/1993 |
| WO | WO 94/20073 | 9/1994 |
| WO | WO 94/26764 | 11/1994 |
| WO | WO 96/10391 | 4/1996 |
| WO | WO 96/40062 | 12/1996 |
| WO | WO 97/04787 | 2/1997 |
| WO | WO 97/12896 | 4/1997 |
| WO | WO 97/13499 | 4/1997 |
| WO | WO 97/30731 | 8/1997 |
| WO | WO 98/39352 | 9/1998 |
| WO | WO 99/14226 | 3/1999 |
| WO | WO 00/56746 | 9/2000 |
| WO | WO 00/56748 | 9/2000 |
| WO | WO 00/66604 | 11/2000 |
| WO | WO 01/00641 | 1/2001 |
| WO | WO 01/07455 | 2/2001 |
| WO | WO 2004/016274 | 2/2004 |

OTHER PUBLICATIONS

U.S. Appl. No. 08/886,829, filed Jul. 1, 1997, Teng et al.
U.S. Appl. No. 09/082,624, filed May 21, 1998, Teng et al.
U.S. Appl. No. 09/256,515, filed Feb. 23, 1999, Hardee et al.
U.S. Appl. No. 09/315,298, filed May 20, 1999, Teng et al.
Adams et al., "Hindered Dialkylamino Nucleoside Phosphite Reagents in the Synthesis of Two DNA 51-Mers," *J. Am. Chem. Soc.* 105:661-663 (1983).
Allen et al., "Large Unilamellar Liposomes with Low Uptake Into the Reticuloendothelial System," *FEBS Lett.* 223:42-46 (1987).
Andres et al., "New 4'-Functionalized 2,2':6',2"-Terpyridines for Applications in Macromolecular Chemistry and Nanoscience," *Eur. J. Org. Chem.* 19:3769-3776 (2003).
Babu et al., "Optimized DNA Targeting Using N,N-Bis(2-Pyridylmethyl)-β-Alanyl 2'- Amino-LNA," *Chem. Commun.* Issue 13, pp. 1705-1707 (2005).

(Continued)

*Primary Examiner* — Tracy Vivlemore
(74) *Attorney, Agent, or Firm* — Clark & Elbing LLP; Kristina Bieker-Brady

(57) ABSTRACT

The present invention relates to novel modified oligomeric compounds and to methods of making and using such compounds. The invention further relates to methods of enhancing the cellular uptake of oligomeric compounds comprising conjugating a metal chelator to those.

10 Claims, 4 Drawing Sheets

OTHER PUBLICATIONS

Figure 1:
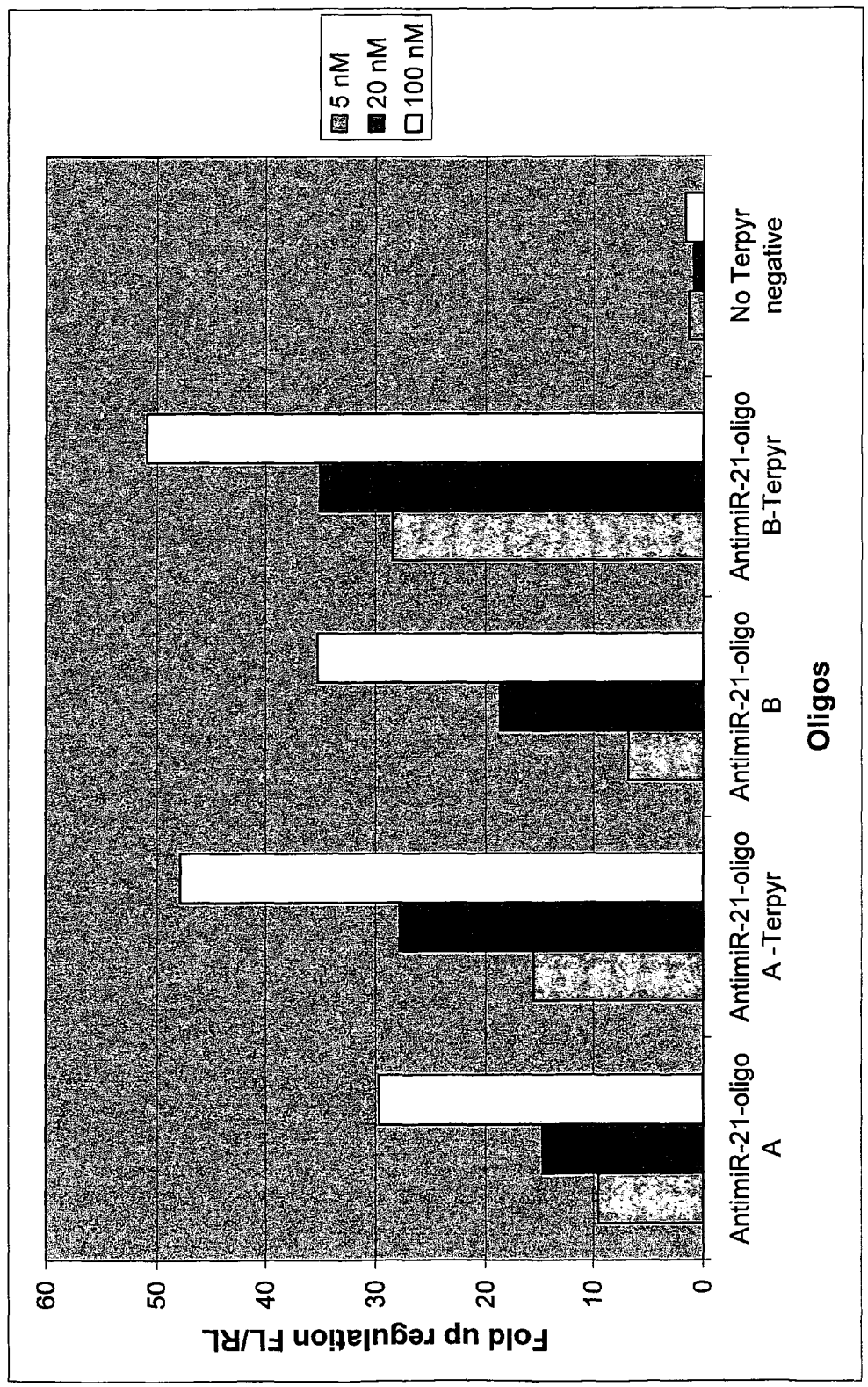

Berge et al., "Pharmaceutical Salts," *J. Pharm. Sci.* 66:1-19 (1977).
Blume et al., "Liposomes for the Sustained Drug Release in Vivo," *Biochim. Biophys. Acta* 1029:91-97 (1990).
Buur et al., "Penetration of 5-Fluorouracil and Prodrugs Across the Intestine of the Albino Rabbit: Evidence for Shift in Absorption Site from the Upper to Lower Region of the Gastrointestinal Tract by Prodrugs," *Journal of Controlled Release* 14:43-51 (1990).
Caruthers et al., "Chemical Synthesis and Biological Studies on Mutated Gene-Control Regions," *Cold Spring Harbor Symp. Quant. Biol.* 47(Pt. 1):411-418 (1983).
Constantinides et al., "Formulation and Intestinal Absorption Enhancement Evaluation of Water-in-Oil Microemulsions Incorporating Medium-Chain Glycerides," *Pharm. Res.* 11:1385-1390 (1994).
Cook, "Medicinal Chemistry of Antisense Oligonucleotides-Future Opportunities," *Anti-Cancer Drug Design* 6:585-607 (1991).
Dheur et al., "Polyethylenimine but Not Cationic Lipid Improves Antisense Activity of 3'-Capped Phosphodiester Oligonucleotides," *Antisense Nucleic Acid Drug Dev.* 9:515-525 (1999).
du Plessis et al., "Topical Delivery of Liposomally Encapsulated Gamma-Interferon," *Antiviral Res.* 18:259-265 (1992).
El-Hariri et al., "The Mitigating Effects of Phosphatidylcholines on Bile Salt- and Lysophospatidycholine-Induced Membrane Damage," *J. Pharm. Pharmacol.* 44:651-654 (1992).
Englisch et al., "Chemically Modified Oligonucleotides as Probes and Inhibitors," *Angew. Chem. Int. Ed. Engl.* 30:613-629 (1991).
Freier et al., "The Ups and Downs of Nucleic Acid Duplex Stability: Structure-Stability Studies on Chemically Modified DNA:RNA Duplexes," *Nuc. Acids Res.* 25:4429-4443 (1997).
Füssl et al., "Cellular Uptake of PNA-Terpyridine Conjugates and Its Enhancement by $Zn^{2+}$ Ions," *J. Am. Chem. Soc.* 128:5986-5987 (2006).
Gabizon et al., "Liposome Formulations with Prolonged Circulation Time in Blood and Enhanced Uptake by Tumors," *Proc. Natl. Acad. Sci. U.S.A.* 85:6949-6953 (1988).
Gait, "Peptide-Mediated Cellular Delivery of Antisense Oligonucleotides and Their Analogues," *Cell. Mol. Life Sci.* 60:844-853 (2003).
Gall et al., "Formation and Detection of RNA-DNA Hybrid Molecules in Cytological Preparations," *Proc. Natl. Acad. Sci. U.S.A.* 63:378-383 (1969).
Guckian et al., "Factors Contributing to Aromatic Stacking in Water: Evaluation in the Context of DNA," *J. Am. Chem. Soc.* 122:2213-2222 (2000).
Håkansson et al., "Convenient Synthesis of 7-Hydrox-1-(Hydroxymethyl)-3-(Thymin-1-yl)-2,5-Dioxabicyclo[2.2.1]Heptanes: α-L-Ribo- and α-L-Xylo-Configured LNA Nucleosides," *J.Org. Chem.* 65:5161-5166 (2000).
Håkansson et al., "The Adenine Derivative of α-L-LNA (α-L-*Ribo* Configured Locked Nucleic Acid): Synthesis and High-Affinity Hybridization Towards DNA, RNA, LNA, and αL-LNA Complementary Sequences," *Bioorg. Med. Chem. Lett.* 11:935-938 (2001).
Ho et al., "Preparation of Microemulsions Using Polyglycerol Fatty Acid Esters as Surfactant for the Delivery of Protein Drugs," *J. Pharm. Sci.* 85:138-143 (1996).
Hu et al., "Topical Delivery of Cyclosporine A from Non-Ionic Liposomal Systems: An In Vivo/In Vitro Correlation Study Using Hairless Mouse Skin," *S.T.P. Pharma Sci.* 4:466-469 (1994).
Illum et al., "The Organ Uptake of Intravenously Administered Colloidal Particles Can be Altered Using a Non-Ionic Surfactant (Poloxamer 338)," *FEBS Lett.* 167:79-82 (1984).
Inoue et al., "Efficient Site-Specific Cleavage of RNA Using a Terpyridine-Copper(II) Complex Joined to a 2'-O-Methyloligonucleotide by a Non-Flexible Linker," *Chem. Commun.* Issue 1, pp. 45-46 (1999).
Jarrett, "Affinity Chromatography with Nucleic Acid Polymers," *J. Chromatography* 618:315-339 (1993).
John et al., "RNA-DNA Hybrids at the Cytological Level," *Nature* 223:582-587 (1969).

Klibanov et al., "Amphipathic Polyethyleneglycols Effectively Prolong the Circulation Time of Liposomes," *FEBS Lett.* 268:235-237 (1990).
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron* 54:3607-3630 (1998).
Koshkin et al., "A Simplified and Efficient Route to 2'-O, 4'-C-Methylene-Linked Bicyclic Ribonucleosides (Locked Nucleic Acid)," *J. Org. Chem.* 66:8504-8512 (2001).
Kren et al., "Correction of the UDP-Glucuronosyltransferase Gene Defect in the Gunn Rat Model of Crigler-Najjar Syndrome Type I with a Chimeric Oligonucleotide," *Proc. Natl. Acad. Sci. U.S.A.* 96:10349-10354 (1999).
Kroschwitz (Ed.), Concise Encyclopedia of Polymer Science and Engineering, John Wiley & Sons, pp. 858-859 (1990).
Kumar et al., "The First Analogues of LNA (Locked Nucleic Acids): Phosphorothioate-LNA and 2'-Thio-LNA," *Bioorg. Med. Chem. Lett.* 8:2219-2222 (1998).
Kværnø et al., "Synthesis of Abasic Locked Nucleic Acid and Two *Seco*-LNA Derivatives and Evaluation of Their Hybridization Properties Compared with Their More Flexible DNA Counterparts," *J. Org. Chem.* 65:5167-5176 (2000).
Kværnø et al., "Novel Bicyclic Nucleoside Analogue (1$S$,5$S$,6$S$)-6-Hydroxyl-5-Hydroxymethyl-1-(Uracil-1-yl)-3,8-Dioxabicyclo[3.2.1]Octane: Synthesis and Incorporation into Oligodeoxynucleotides," *J. Org. Chem.* 66:5498-5503 (2001).
Lee et al., "Mucosal Penetration Enhancers for Facilitation of Peptide and Protein Drug Absorption," *Crit. Rev. Ther. Drug Carrier Systems* 8:91-192 (1991).
Lindsay, "Peptide-Mediated Cell Delivery: Application in Protein Target Validation," *Curr. Opin. Pharmacol.* 2:587-594 (2002).
Mattick, "Non-Coding RNAs: The Architects of Eukaryotic Complexity," *EMBO Rep.* 2:986-991 (2001).
Mesmaeker et al., "Backbone Modifications in Oligonucleotides and Peptide Nucleic Acid Systems," *Curr. Opin. Structural Biol.* 5:343-355 (1995).
Miyao et al., "Stability and Pharmacokinetic Characteristics of Oligonucleotides Modified at Terminal Linkages in Mice," *Antisense Res. Dev.* 5:115-121 (1995).
Morita et al., "2'-O,4'-C-Ethylene-Bridged Nucleic Acids (ENA): Highly Nuclease-Resistant and Thermodynamically Stable Oligonucleotides for Antisense Drug," *Bioorg. Med. Chem. Lett.* 12:73-76 (2002).
Muranishi, "Absorption Enhancers," *Critical Rev. Therap. Drug Carrier Systems* 7:1-33 (1990).
Okazaki et al., "Analysis of the Mouse Transcriptome Based on Functional Annotation of 60,770 Full-Length cDNAs," *Nature* 420:563-573 (2002).
Papahadjopoulos et al., "Targeting of Liposomes to Tumor Cells in Vivo," *Ann. N.Y. Acad. Sci.* 507:64-74 (1987).
Pfundheller et al., "Evaluation of Oligonucleotides Containing Two Novel 2'-O-Methyl Modified Nucleotide Monomers: A 3'-C-Allyl and a 2'-O, 3'-C-Linked Bicyclic Derivative," *Nucleosides and Nucleotides* 18:2017-2030 (1999).
Putnam et al., "De Novo Synthesis of Artificial Ribonucleases with Benign Metal Catalysts," *Chem. Commun.* Issue 9, pp. 767-768 (2000).
Ritschel, "Microemulsions for Improved Peptide Absorption from the Gastrointestinal Tract," *Meth. Find. Exp. Clin. Pharmacol.* 13:205-220 (1991).
Rosenbohm et al., "Synthesis of 2'-Amino-LNA: A New Strategy," *Org. Biomol. Chem.* 1:655-663 (2003).
Sanghvi, "Chapter 15: Heterocyclic Base Modifications in Nucleic Acids and Their Applications in Antisense Oligonucleotides," In Antisense Research and Applications, Crooke and Lebleu (Eds.), CRC Press, pp. 273-288 (1993).
Singh et al., "LNA (Locked Nucleic Acids): Synthesis and High-Affinity Nucleic Acid Recognition," *Chem. Commun.* Issue 4, pp. 455-456 (1998).
Singh et al., "Synthesis of Novel Bicyclo[2.2.1]Ribonucleosides: 2'-Amino- and 2'-Thio-LNA Monomeric Nucleosides," *J. Org. Chem.* 63:6078-6079 (1998).

Singh et al., "Synthesis of 2'-Amino-LNA: A Novel Conformationally Restricted High-Affinity Oligonucleotide Analogue with a Handle," *J. Org. Chem.* 63:10035-10039 (1998).

Sunamoto et al., "Liposomal Membranes. V. Interaction of Zinc(II) Ion with Egg Phosphatidylcholine Liposomes," *Bull. Chem. Soc. Jpn.* 53:2778-2781 (1980).

Takahashi et al., "The Use of a Perfluorochemical Emulsion as a Vascular Perfusate in Drug Absorption," *J. Pharm. Pharmacol.* 40:252-257 (1988).

Takakura et al., "Uptake Characteristics of Oligonucleotides in the Isolated Rat Liver Perfusion System," *Antisense Nucleic Acid Drug Dev.* 6:177-183 (1996).

Wadia et al., "Protein Transduction Technology," *Curr. Opin. Biotechnol.* 13:52-56 (2002).

Wahlestedt et al., "Potent and Nontoxic Antisense Oligonucleotides Containing Locked Nucleic Acids," *Proc. Natl. Acad. Sci. U.S.A.* 97:5633-5638 (2000).

Wang et al., "Plasmid DNA Absorbed to pH-Sensitive Liposomes Efficiently Transforms the Target Cells," *Biochem. Biophys. Res. Comm.* 147:980-985 (1987).

Weiner et al., "Liposomes: A Novel Topical Delivery System for Pharmaceutical and Cosmetic Applications," *J. Drug Targeting* 2:405-410 (1994).

Wu et al., "Increased Microvascular Permeability Contributes to Preferential Accumulation of Stealth Liposomes in Tumor Tissue," *Cancer Res.* 53:3765-3770 (1993).

Yamamoto et al., "A Mechanistic Study on Enhancement of Rectal Permeability to Insulin in the Albino Rabbit," *J. Pharmacol. Exp. Ther.* 263:25-31 (1992).

Yamashita et al., "Effects of Diclofenac Sodium and Disodium Ethylenediaminetetraacetate on Electrical Parameters of the Mucosal Membrane and Their Relation to the Permeability Enhancing Effects in the Rat Jejunum," *J. Pharm. Pharmacol.* 39:621-626 (1987).

Yamashita et al., "Effects of Adjuvants on Charge-Selective Permeability and Electrical Resistance of Rat Jejunal Membrane," *J. Pharm. Sci.* 79:579-583 (1990).

Yelin et al., "Widespread Occurrence of Antisense Transcription in the Human Genome," *Nature Biotechnol.* 21:379-386 (2003).

Zhou et al., "Targeted Delivery of DNA by Liposomes and Polymers," *J. Controlled Release* 19:269-274 (1992).

International Search Report for PCT/DK2008/000019, completed Oct. 27, 2008, mailed Nov. 5, 2008.

International Preliminary Report on Patentability for PCT/DK2008/000019, issued Jul. 21, 2009.

Written Opinion of the International Searching Authority for PCT/DK2008/000019, completed Oct. 27, 2008, mailed Nov. 5, 2008.

El-Hariri et al., "The Mitigating Effects of Phosphatidylcholines on Bile Salt- and Lysophosphatidylcholine-Induced Membrane Damage," *J. Pharm. Pharmacol.* 44:651-654, 1992.

Rosenbohm et al., "Synthesis of 2'-Amino-LNA: A New Strategy," *Org. Biomol. Chem.* 1:655-663, 2003.

* cited by examiner

MEDIATED CELLULAR DELIVERY OF LNA OLIGONUCLEOTIDES

Cross-reference to Related Applications

This application is the U.S. National Stage of International Application No. PCT/DK2008/000019, filed Jan. 18, 2008, which, in turn, claims the benefit of Danish Patent Application Number PA200700087, filed Jan. 19, 2007.

The present invention relates to novel modified oligomeric compounds and to methods of making and using such compounds. The invention further relates to methods of enhancing the cellular uptake of oligomeric compounds comprising conjugating a metal chelator to those.

SUMMARY OF THE INVENTION

The present invention relates to oligomeric compounds having a metal chelator covalently conjugated thereto. The metal chelator enhances functional cellular uptake of the oligomeric compounds compared to its native counterpart. The present invention can be used in combination with other known moieties that enhances cellular uptake. The oligomeric compounds can be used to direct specific inhibition, degradation or thethering of other functional groups to their target RNAs and DNAs, both coding and non-coding.

BACKGROUND OF THE INVENTION

A general object of some current therapeutic approaches is to interfere with, or otherwise modulate, gene expression.

One method for inhibiting the expression of specific genes involves the use of oligonucleotides, particularly oligonucleotides that are complementary to a specific target messenger RNA (mRNA) sequence, known as antisense oligonucleotides. Several oligonucleotides are currently undergoing clinical trials for such use.

Oligonucleotides and their analogs can be designed to have particular properties. A number of chemical modifications have been introduced into oligomeric compounds to increase their usefulness as therapeutic agents. Such modifications include those designed to increase binding affinity to a target strand, to increase cell penetration, to stabilize against nucleases and other enzymes that degrade or interfere with the structure or activity of the oligonucleotide, to provide a mode of disruption (terminating event) once the oligonucleotide is bound to a target, and to improve the pharmacokinetic properties of the oligonucleotide. Despite such modifications, the cellular uptake of oligomeric compounds remains poor.

Oligonucleotides have been formulated with various with transfection agents, including anionic and cationic lipids and polyamines, in an attempt to improve their ability to permeate biological membranes. Of the transfection agents used, polyethylenimines (PEI) are generally the most efficient and least expensive delivery vehicles. Kren, B. T.; Parashar, B.; Bandyopadhyay, P.; Chowdhury, N. R.; Chowdhury, J. R.; Steer, C. J. Proc. Natl. Acad. Sci. U.S.A. 1999, 96, 10349-10354. It was observed, however, that, although complexes of excess PEI and oligonucleotide phosphorothioates were efficiently taken up by cells, the oligonucleotides failed to dissociate in the cytoplasm, resulting in no appreciable enhancement in the antisense activity of the oligonucleotides. Dheur, S.; Dias, N.; Van Aerschot, A.; Herdewijn, P.; Bettinger, T.; Remy, J.-S.; Helene, C.; Saison-Behmoaras, E. T. Antisense Nucleic Acid Drug Dev. 1999, 9, 515-525.

Another approach has been attempts to enhance the cellular uptake of oligomeric compounds comprising conjugating the compounds to amphipathic moieties such as amphipathic peptides. (PCT Publication WO 2004/016274).

Conjugation of terpyridine to PNA nucleotides have previously been shown to mediate cellular uptake of a PNA oligonucleotide as monitored by fluorescence. This process was suggested to be dependent on $Zn^{2+}$ chelating. These experiments were carried out in HeLa cells using elevated concentrations (1-2.5 µM) of fluorophor labeled oligonucleotides added directly to the cell culture media. Addition of high concentrations of oligonucleotides usually leads to some uptake, probably through so called phase fluid endocytosis, as can be observed as a punctuated intracellular distribution, mostly located to endosomes. Interestingly conjugation of terpyridine to PNA led to increased nuclear localization of the oligo, indicating that oligonucleotide may be free to base pair with a potential target sequence, however, no such data was presented (Andreas Fuss, Andreas Schleifenbaum, Mareike Göritz, Andrew Riddel, Carsten Schultz, Roland Krämer, J. Am. Chem. Soc. 2006, 128(8), 5986-5987.)

A need therefore exists in the art for the development of means to improve the cellular uptake and cellular distribution of oligomeric compounds.

RNA-mediated gene regulation is widespread in higher eukaryotes and complex genetic phenomena like RNA interference, co-suppression, transgene silencing, imprinting, methylation, and possibly position-effect variegation and transvection, all involve intersecting pathways based on or connected to RNA signalling (Mattick 2001; EMBO reports 2, 11: 986-991). Recent studies indicate that antisense transcription is a very common phenomenon in the mouse and human genomes (Okazaki et al. 2002; Nature 420: 563-573; Yelin et al. 2003, Nature Biotechnol.). Thus, antisense modulation of gene expression in eukaryotic cells, e.g. human cells appear to be a common regulatory mechanism. In light of this, the present invention provides a method for detection and functional analysis of non-coding antisense RNAs, as well as a method for detecting the overlapping regions between sense-antisense transcriptional units.

SUMMARY OF THE INVENTION

The present invention relates to metal chelating agents (such as 2,2':6',2'-terpyridine (terpyridine)) facilitating the delivery of a wide variety of modified oligonucleotides both ex vivo and in vivo.

In certain embodiments the conjugation of metal chelating agents is used for the modification of LNA-modified oligonucleotides, particularly when the oligonucleotides are used for delivery of miRNA knockdown oligonucleotides, in particular for enabling knockdown studies in hard-to-transfect cell lines and primary culture.

The invention provides for an oligonucleotide composition optionally substituted with one or more metal chelators. In a preferred embodiment, at least one non-natural monomer of the oligonucleotide composition is substituted with one or more metal chelators.

The present invention in one aspect provides for a compound of formula I:

OLIGO-L-CHEL         (I)

wherein "OLIGO" designates an oligonucleotide composition, "CHEL" designates a metal chelator and "L" is a linking moiety consisting of from 1 to 6 consecutive groups of the formula —$(CR^1R^2)_w Y_z$—, wherein $R^1$ and $R^2$ are separately hydrogen or a heteroatom such as O, S, Se, O, Si, N, P; or a $C_1$-$C_{20}$ alkyl group optionally substituted with one or more heteroatoms such as oxygen atoms, nitrogen atoms, and/or sulphur atoms, optionally containing aromatic or mono/poly-unsaturated hydrocarbons, polyoxyethylene such as polyethylene glycol, oligo/polyamides such as poly-β-alanine, polyglycine, polylysine, peptides, oligo/polysaccharides; or $R^1$ and $R^2$ are separately forming a double bond to the carbon;
W is an integer of from 0 and up;
Y is a heteroatom such as O, S, Se, O, Si, N, P, to which hydrogen, alkyl, allyl, aromates, carbocycles or other heteroatoms are attached;
Z is an integer from 0 and up;
and wherein the consecutive groups can be the same or different.

Examples of a $C_1$-$C_{20}$ alkyl group include a straight chain, branched chain or cyclic alkyl group such as a methyl, ethyl, n-propyl, isopropyl, n-butyl, isobutyl, sec-butyl, tert-butyl, n-pentyl, n-decyl, cyclopropyl, 2,2-dimethylcyclopropyl, cyclopentyl, cyclohexyl and menthyl group.

In a further aspect the present invention relates to compounds as described above with an antisense, silencing or knock-down efficacy.

The present invention furthermore provides for a method of synthesising a compound of formula I, comprising the following steps:
a) coupling a linker moiety with a suitable solid phase protecting group to the 5'-end of an oligonucleotide composition by a conventionally used process,
b) cleaving off said protecting group using a suitable reagent,
c) conjugating to said linker moiety a methal chelator, and
d) deprotecting said oligonucleotide composition.

In an additional embodiment, the invention provides a method of synthesising a compound of formula I, comprising the following steps:
a) attaching a linker moiety to the solid phase by conventionally used processes, thereby attaching the linker to the 3'-end of an oligonucleotide,
b) synthesising an oligonucleotide composition using conventionally used processes,
c) deprotecting said oligonucleotide composition, and
d) conjugating to said linker moiety a metal chelator.

The invention further provides for kits comprising a compound of formula I for use in diagnostics.

A further aspect of the present invention is the use of any of the above mentioned compounds for the treatment of a disease.

FIGURES

FIG. 1 shows the effect on MCF7 cells of co-transfection with pMIR-21 (hsa-miR-21 firefly luciferase reporter construct) and the indicated miR-21 inhibiting oligonucleotides with or without terpyridine conjugates. The diagram shows fold up regulation; FL (RLU)/RL (RLU). Relative light units (RLU); firefly luminescence (FL); Renilla luminescence (RL).

Figure 2:
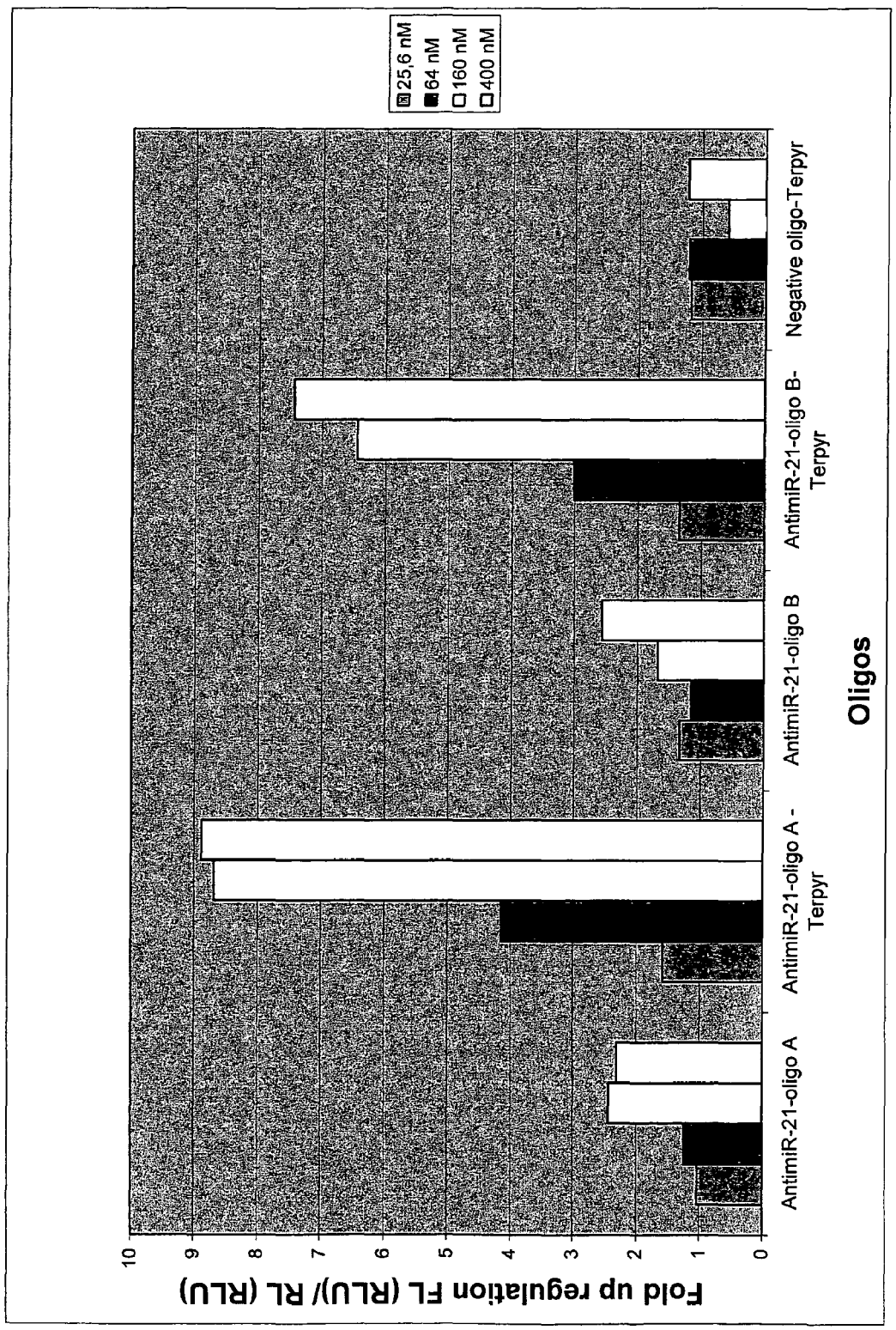

FIG. 2 shows the effect of terpyridine conjugation in absence of transfection reagent. The diagram shows fold up regulation; FL (RLU)/RL (RLU). Relative light units (RLU); firefly luminescence (FL); Renilla luminescence (RL). Relative light units (RLU); firefly luminescence (FL); Renilla luminescence (RL).

Figure 3:
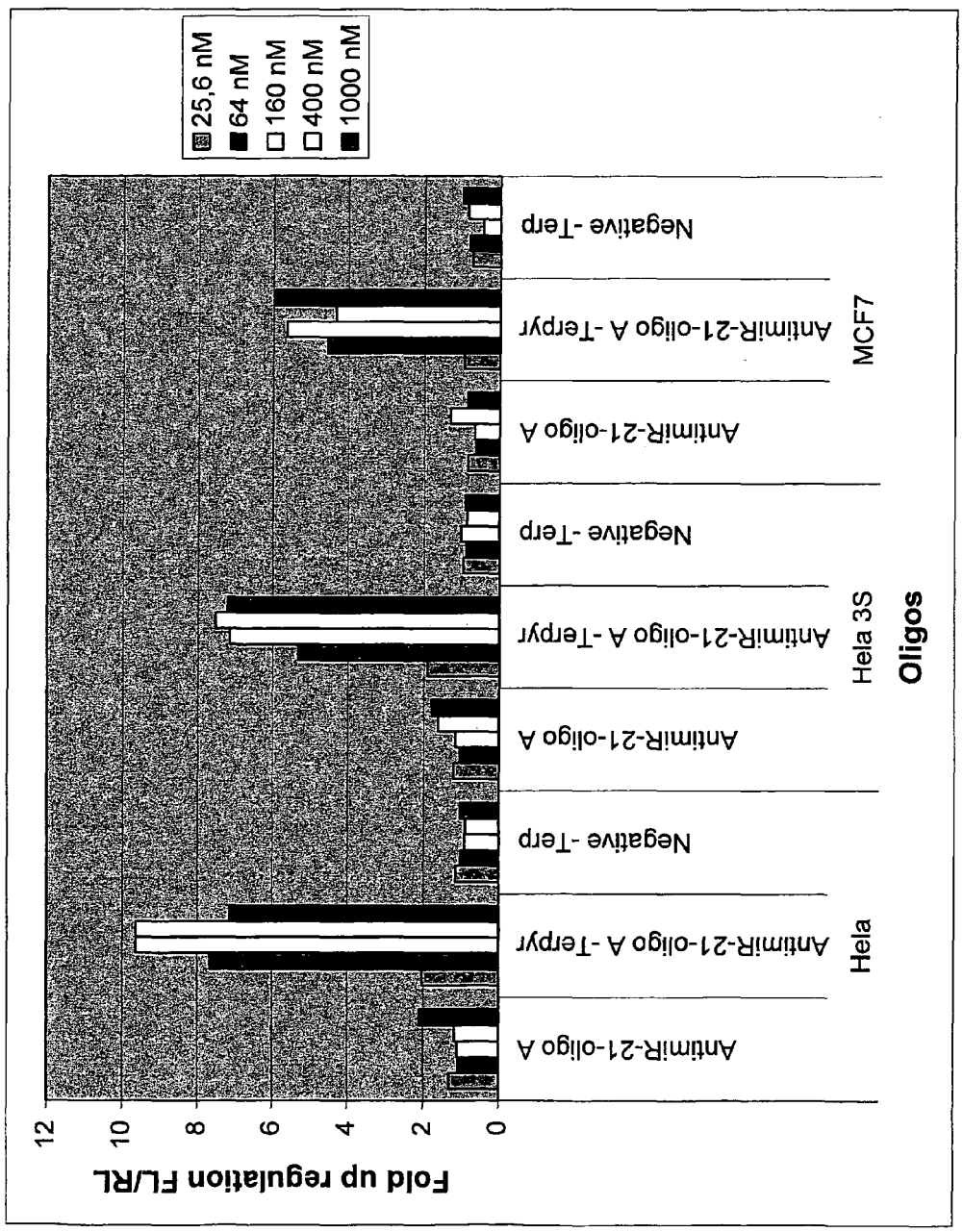

FIG. 3 shows the effect of terpyridine conjugation in absence of transfection reagent in HeLa, HeLa 3S, and MCF7 cells. The diagram shows fold up regulation of FL (RLU)/RL (RLU). Relative light units (RLU); firefly luminescence (FL); Renilla luminescence (RL).

Figure 4:
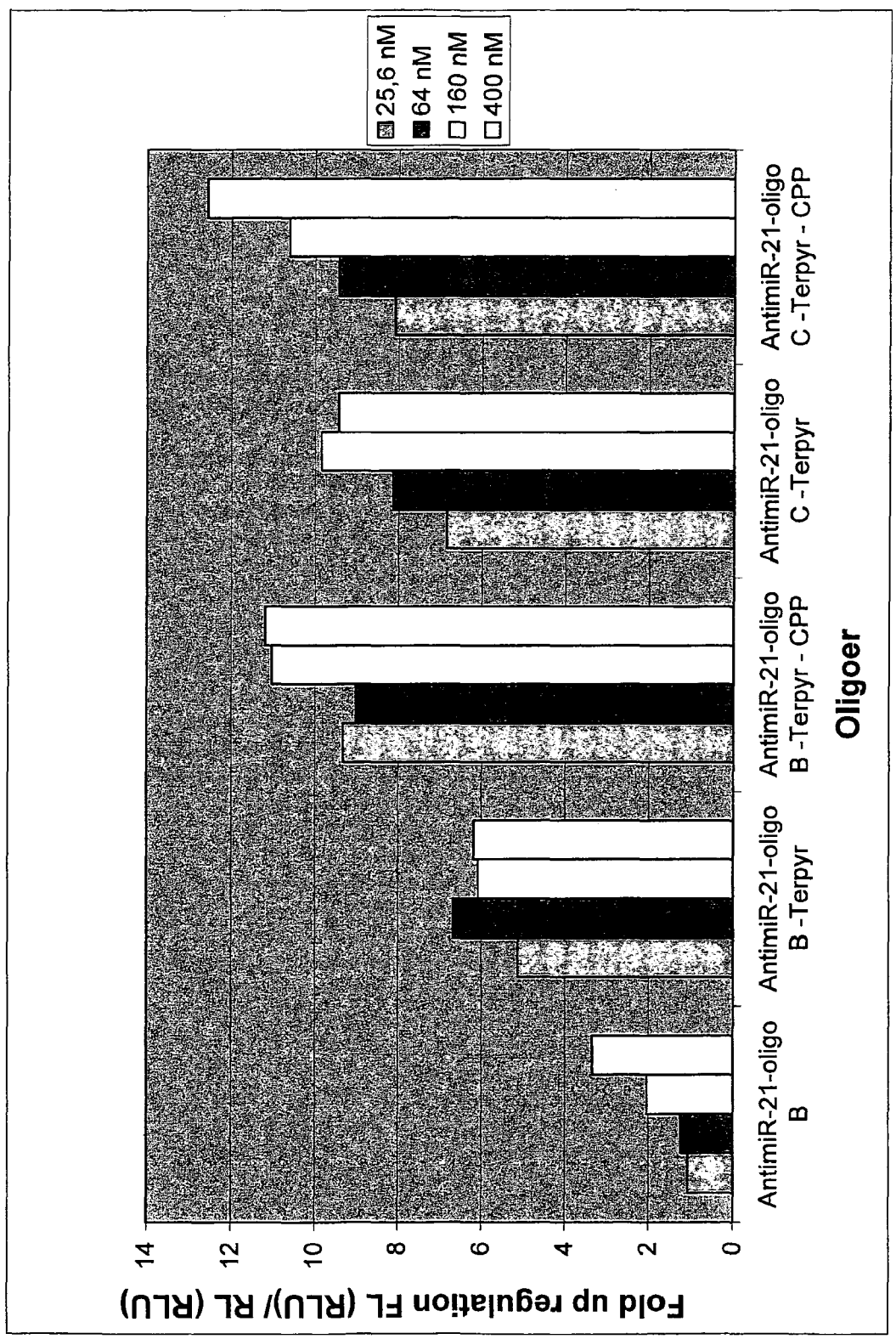

FIG. 4 shows the effect of terpyridine-CPP conjugation in absence of transfection reagent in HeLa cells. The diagram shows fold up regulation of FL (RLU)/RL (RLU). Relative light units (RLU); firefly luminescence (FL); Renilla luminescence (RL).

DETAILED DESCRIPTION OF THE INVENTION

In a particular embodiment of the invention oligonucleotides are referred to as "oligonucleotide compositions".

"Oligonucleotide compositions" are oligonucleotides wherein at least one monomer is a non-natural nucleotide also designated a "modified monomer unit", which preferably is a LNA monomer as defined below and the remaining monomers are natural nucleotides. Preferred LNA monomers are oxy-LNA, alpha-LNA and amino-LNA as defined below.

A "reference oligonucleotide composition" is a "oligonucleotide composition" as defined above wherein one or more non-natural nucleotide, preferably a LNA monomer is replaced with a natural nucleotide.

An example of an oligonucleotide composition of the invention and the corresponding reference oligonucleotide composition are shown in Table 1

TABLE 1

| | |
|---|---|
| Target sequence (microRNA-hsa-miR-21) | 5'-uagcuuaucagacugauguga-3' (SEQ ID NO: 1) |
| oligonucleotide composition | Terp-tmCaamCatmCagTctGatAagmCta (SEQ ID NO: 2) |
| Reference oligonucleotide composition | TmCaamCatmCagTctGatAagmCta (SEQ ID NO: 3) |

Abbreviations:
Capital G, A, T, or mC letters indicates oxy-LNA
Lowercase indicates natural DNA/RNA
mC indicates 5-methylcytosine
Terp indicates terpyridine introduced at the 5'-end Oligonucleotide compositions and reference oligonucleotide compositions shown in Table 1 is based on the reverse complementary sequence of the microRNA hsa-miR-21 (miRBase accession number MIMAT0000076).

The present invention also provides a kit for detection of nucleic acids. The present invention also provides a kit for sequence specific inactivation of intracellular nucleic acids. The present invention also provides a kit for introduction of nucleic acids to a cell.

For the kits according to the invention, the reaction body is preferably a solid support material, e.g. selected from borosilicate glass, soda-lime glass, polystyrene, polycarbonate, polypropylene, polyethylene, polyethyleneglycol terephthalate, polyvinylacetate, polyvinylpyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a microtitre plate, a stick, or a multi-bladed stick.

A written instruction sheet stating the optimal conditions for use of the kit typically accompanies the kits.

LNA substituted oligomers are preferably chemically synthesized using commercially available methods and equipment as described in the art (Koshkin et al., *Tetrahedron* 54:

3607-30, 1998). For example, the solid phase phosphoramidite method can be used to produce short LNA probes (Caruthers, et al., *Cold Spring Harbor Symp. Quant. Biol.* 47:411-418, 1982, Adams, et al., *J. Am. Chem. Soc.* 105: 661 (1983).

Suitable samples of target nucleic acid molecules may comprise a wide range of eukaryotic and prokaryotic cells or other biological materials, which may harbour target nucleic acids. The methods are thus applicable to systemic delivery in metazoans, to tissue culture of animal cells (e.g., fibroblasts, lymphocytes, embryonic stem cells, osteoblasts, neurons, oocytes), any type of tissue biopsy/explant (e.g. a muscle biopsy, a liver biopsy, a kidney biopsy, a bladder biopsy, a bone biopsy, a cartilage biopsy, a skin biopsy, a pancreas biopsy, a biopsy of the intestinal tract, a thymus biopsy, a mammae biopsy, a uterus biopsy, a testicular biopsy, an eye biopsy or a brain biopsy)), plant cells, bacteria, yeasts, viruses, mycoplasmas, protozoa, rickettsia, fungi and other small microbial cells and the like.

DETAILED DESCRIPTION OF THE PREFERRED EMBODIMENTS

In the context of this invention, the term "oligomeric compound" refers to a polymeric structure capable of hybridizing a region of a nucleic acid molecule. This term includes oligonucleotides, oligonucleosides, oligonucleotide analogs, modified oligonucleotides and oligonucleotide mimetics. Oligomeric compounds can be prepared to be linear or circular and may include branching. They can be prepared single stranded or double stranded and may include overhangs. In general an oligomeric compound comprises a backbone of linked momeric subunits where each linked momeric subunit is directly or indirectly attached to a heterocyclic base moiety. The linkages joining the monomeric subunits, the monomeric subunits and the heterocyclic base moieties can be variable in structure giving rise to a plurality of motifs for the resulting oligomeric compounds including hemimers, gapmers and chimeras.

Oligomeric compounds according to the present invention preferably comprise from about 5 to about 50 monomer subunits and, hence, about 5 to about 50 nucleosidic bases. It is more preferred that such compounds comprise from about 8 to about 30 monomer subunits, with 15 to 25 monomer subunits being particularly preferred. In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The terms "oligonucleotide analog" and "modified oligonucleotide" refers to oligonucleotides that have one or more non-naturally occurring portions which function in a similar manner to oligonulceotides. Such modified or substituted oligonucleotides are often preferred over native forms because of desirable properties such as, for example, enhanced cellular uptake, enhanced affinity for nucleic acid target and increased stability in the presence of nucleases.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure. However, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

In the context of this invention, the term "oligonucleotide mimetic" refers to an oligonucleotide wherein the backbone of the nucleotide units has been replaced with groups of somewhat equivalent function. Although the term is intended to include oligomeric compounds wherein only the furanose ring or both the furanose ring and the internucleotide linkage are replaced with novel groups, replacement of only the furanose ring is also referred to in the art as being a sugar surrogate. Oligonucleotide mimetics can be further modified to incorporate one or more modified heterocyclic base moieties to enhance properties such as hybridization.

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methelyne ($-CH_2-$)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C.), stability towards 3'-exonucleolytic degradation and good solubility properties. The basic structure of LNA showing the bicyclic ring system is shown below Novel types of LNA-modified oligonucleotides, as well as the LNAs, are useful in a wide range of diagnostic and therapeutic applications. Among these are antisense applications, PCR applications, as strand-displacement oligomers, as substrates for nucleic acid polymerases and generally as nucleotide based drugs.

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The oligomeric compound conjugates in accordance with the invention can be used in diagnostics, therapeutics and as research reagents and kits. The compounds can be used in pharmaceutical compositions by including a suitable pharmaceutically acceptable diluent or carrier. They can further be used for treating organisms having a disease characterized by the undesired production of a protein. The organism should be contacted with an oligomeric compound conjugate having an oligonucleotide sequence that is capable of specifically hybridizing with a strand of nucleic acid encoding the undesirable protein or a strand of nucleic acids regulating the encoding nucleic acid strand of the protein of interest. Such oligonucleotide could direct cleavage steric hindrance of the protein encoding strand or it could form triplex structures with double stranded genomic DNA, likewise for steric hindrance, cleavage or tethering of functional moieties and proteins. Treatments of this type can be practiced on a variety of organisms ranging from unicellular prokaryotic and eukaryotic organisms to multicellular eukaryotic organisms. Any organism that utilizes DNA-RNA transcription, RNA-protein translation or miRNA/shRNA/piRNA/aRNA regulating mechanism as a fundamental part of its hereditary, metabolic or cellular control is susceptible to therapeutic and/or prophylactic treatment in accordance with the invention. Seemingly diverse organisms such as bacteria, yeast, protozoa, algae, plants and higher animal forms, including warm-blooded animals, can be treated. Further, each cell of multicellular eukaryotes can be treated, as such cells carry out both DNA-RNA transcription and RNA-protein translation as integral parts of their activity. Furthermore, many of the organelles (e.g., mitochondria and chloroplasts) of eukaryotic cells also include transcription and translation mechanisms. Thus, single cells, cellular populations, or organelles can also be included within the definition of organisms that can be treated with therapeutic or diagnostic oligonucleotides.

For therapeutics, an animal, preferably a human, suspected of having a disease or disorder which can be treated by modulating the target sequence is treated by administering oligomeric compound conjugates in accordance with this invention. The oligomeric compound conjugates of the invention can be utilized in pharmaceutical compositions by adding an effective amount of the oligomeric compound conjugates to a suitable pharmaceutically acceptable diluent or carrier. Use of the oligomeric compound conjugates and methods of the invention may also be useful prophylactically, e.g., to prevent or delay infection, inflammation or tumor formation, for example.

The oligomeric compound conjugates of the invention are useful for research and diagnostics, because these compounds can be prepared to hybridize to nucleic acids encoding a particular protein or miRNA/piRNA/shRNA, aRNA regulating the encoding nucleic acids, enabling sandwich and other assays to easily be constructed to exploit this fact. Hybridization of the oligomeric compound conjugates of the invention with a nucleic acid encoding a particular protein can be detected by means known in the art. Such means may include conjugation of an enzyme to an oligomeric compound conjugate, radiolabelling of the oligomeric compound conjugate, or any other suitable detection means. Kits using such detection means for detecting protein levels in a sample may also be prepared.

The methods of the invention can be used in connection with diagnostics and therapeutics. Methods in accordance with the invention can be used to improve the permeation of biological membranes by therapeutic and diagnostic oligomeric compounds. Further, the methods of the invention can be used to improve the cellular distribution of therapeutic and diagnostic oligomeric compound conjugates once the compounds penetrate biological membranes.

The present invention also includes pharmaceutical compositions and formulations that include the oligomeric compound conjugates of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one LNA modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligomeric compound conjugates of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearoylphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligomeric compound conjugates of the invention may be encapsulated within liposomes or may form complexes thereto, in particular to cationic liposomes. Alternatively, oligomeric compound conjugates may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcamitine, an acylcholine, or a C1-10 alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligomeric compound conjugates of the invention are administered in conjunction with one or more penetration enhancers, surfactants, and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium).

Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligomeric compound conjugates of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyomithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), U.S. application Ser. No. 09/108,673 (filed Jul. 1, 1998), U.S. application Ser. No. 09/256,515 (filed Feb. 23, 1999), U.S. application Ser. No. 09/082,624 (filed May 21, 1998) and U.S. application Ser. No. 09/315,298 (filed May 20, 1999) each of which is incorporated herein by reference in its entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension can also contain stabilizers.

In one embodiment of the present invention, the pharmaceutical compositions are formulated and used as foams. Pharmaceutical foams include formulations such as, but not limited to, emulsions, microemulsions, creams, jellies and liposomes. While basically similar in nature, these formulations vary in the components and the consistency of the final product. The preparation of such compositions and formulations is generally known to those skilled in the pharmaceutical and formulation arts and may be applied to the formulation of the compositions of the present invention.

The compositions of the present invention can be prepared and formulated as emulsions. Emulsions are typically heterogenous systems of one liquid dispersed in another in the form of droplets usually exceeding 0.1 µm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions can contain components in addition to the dispersed phases, and the active drug can be present as a solution in either the aqueous phase, oily phase or as a separate phase. Pharmaceutical excipients such as emulsifiers, stabilizers, dyes, and antioxidants can also be present in emulsions. Pharmaceutical emulsions can also comprise more than two phases, such as, for example oil-in-water-in-oil (o/w/o) and water-in-oil-in-water (w/o/w) emulsions. Such complex formulations often provide advantages that are not achieved with simple binary emulsions. Multiple emulsions in which individual oil droplets of an o/w emulsion enclose small water droplets constitute a w/o/w emulsion. Likewise, a system of oil droplets enclosed in globules of water stabilized in an oily continuous provides an o/w/o emulsion.

Emulsions are characterized by little or no thermodynamic stability. Often, the dispersed or discontinuous phase of the emulsion is dispersed into the external or continuous phase and maintained in this form through the action of emulsifiers or the viscosity of the formulation. Either phase of the emulsion can be a semisolid or a solid, as is the case with emulsion-style ointment bases and creams. Other means of stabilizing emulsions entail the use of emulsifiers that can be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants for the preparation of formulations. Surfactants may be classified based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases, such as anhydrous lanolin and hydrophilic petrolatum, can soak up water to form w/o emulsions, yet retain their semisolid consistencies. Finely divided solids have also been used as emulsifiers, especially in combination with surfactants and in viscous preparations. Such solids include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. Such materials include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335.

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). Hydrocolloids disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, emulsion formulations often incorporate preservatives. Preservatives commonly added to emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants can be free radical scavengers such as tocopherols, alkyl gallates, butylated hydroxyanisole, butylated hydroxytoluene, or reducing agents, such as ascorbic acid and sodium metabisulfite, and antioxidant synergists such as citric acid, tartaric acid, and lecithin.

The application of emulsion formulations via dermatological, oral and parenteral routes, and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation and efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligomeric compound conjugates are formulated as microemulsions. A microemulsion may be defined as a system of water, oil and amphiphile that is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Liebennan, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), and decaglycerol decaoleate (DA0750), alone or in combination with cosurfactants. The cosurfactant, usually a short-chain alcohol such as ethanol, 1-propanol, or 1-butanol, serves to increase the interfacial fluidity by penetrating the surfactant film and creating a disordered film that results from the void space generated among surfactant molecules. Microemulsions can, however, be prepared without the use of cosurfactants, and alcohol-free self-emulsifying microemulsion systems are known in the art. The aqueous phase can include, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are of particular interest from the standpoint of drug solubilization and the enhanced absorption of drugs. It has been proposed that lipid based microemulsions (both o/w and w/o) enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Microemulsions often form spontaneously when their components are brought together at ambient temperature, which may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligomeric compound conjugates from the gastrointestinal tract, as well as improve the local cellular uptake of oligomeric compound conjugates within the gastrointestinal tract, vagina, buccal cavity and other areas of administration.

Microemulsions of the present invention may also contain additional components and additives such as sorbitan monostearate (Grill 3), Labrasol, and penetration enhancers that improve the properties of the formulation and enhance the absorption of the oligomeric compound conjugates of the present invention. Penetration enhancers used in the microemulsions of the present invention may be classified as belonging to one of five broad categories-surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Many organized surfactant structures other than microemulsions exist and have been studied and used for the formulation of drugs. Such structures include monolayers, micelles, bilayers and vesicles. Vesicles, such as liposomes, have attracted great interest due to their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles that have a membrane formed from a lipophilic material and an aqueous interior. The aqueous portion contains the composition to be delivered. Cationic liposomes can fuse to the cell wall. Non-cationic liposomes, although not able to fuse as efficiently with the cell wall, are taken up by macrophages in vivo. In order to cross intact mammalian skin, lipid vesicles must pass through a series of fine pores, each with a diameter less than 50 nm, under the influence of a suitable transdermal gradient. Therefore, it is desirable to use a liposome that is highly deformable and able to pass through such fine pores.

Further advantages of liposomes include biocompatability and biodegradability, the ability to incorporate a wide range of water and lipid soluble drugs, and the ability to protect encapsulated drugs from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size, and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as a mode of delivery for many drugs. Growing evidence indicates that liposomes present several advantages relative to other formulations for topical administration. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes that interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes that are pH-sensitive or negatively-charged entrap DNA, rather than forming a complex with DNA. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome(TM) I (glyceryl dilaurate/cholesterol/polyoxyethylene-10-stearyl ether) and Novasome(TM) II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765). Various liposomes comprising one or more glycolipids are known in the art. Papahadjopoulos et al. (Ann. N.Y. Acad. Sci., 1987, 507, 64) reported the ability of monosialoganglioside GM1, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside GM1 or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, 2C1215G, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates that are attractive candidates for drug delivery vehicles. Transfersomes may be described as lipid droplets that are so highly deformable that they are easily able to penetrate through pores that are smaller than the droplet. Transfersomes are adaptable to the environment in which they are used, e.g. they are self-optimizing (adaptive to the shape of pores in the skin), self-repairing, frequently reach their targets without fragmenting, and are often self-loading. To make transfersomes, surface edge-activators, usually surfactants, are added to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide pH range. In general the HLB values of non-ionic surfactants range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides. The use of surfactants in drug products, formulations and in emulsions has been reviewed (Rieger, in Pharmaceutical Dosage Forms, Marcel Dekker, Inc., New York, N.Y., 1988, p. 285).

In one embodiment, the present invention employs various penetration enhancers to effect the efficient delivery of nucleic acids, particularly oligomeric compound conjugates, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligomeric compound conjugates through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives that act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1-10 alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, N.Y., 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of oligonucleotides through the mucosa is enhanced. With regard to the use of chelating agents as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating, non-surfactant penetration enhancing compounds can be defined as compounds that demonstrate insignificant activity as chelating agents or as surfactants, but that nonetheless enhance absorption of oligomeric compound conjugates through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of oligomeric compound conjugates at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligomeric compounds.

Other agents may be utilized to enhance the penetration of the administered oligomeric compound conjugates, including glycols such as ethylene glycol and propylene glycol, pyrrols such as 2-pyrrol, azones, and terpenes such as limonene and menthone.

Certain compositions of the present invention also incorporate carrier compounds in the formulation. As used herein, "carrier compound" or "carrier" can refer to a nucleic acid, or analog thereof, that is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of an oligomeric compound conjugate and a carrier compound, typically with an excess of the latter substance, can result in a substantial reduction of the amount of oligomeric compound conjugate recovered in the liver, kidney or other extracirculatory reservoirs, presumably due to competition between the carrier compound and the oligomeric compound conjugate for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense Res. Dev., 1995, 5, 115-121; Takakura et al., Antisense & Nucl. Acid Drug Dev., 1996, 6, 177-183).

In contrast to a carrier compound, a "pharmaceutical carrier" or "excipient" is a pharmaceutically acceptable solvent, suspending agent or any other pharmacologically inert vehicle for delivering one or more oligomeric compound conjugates to an animal. The excipient may be liquid or solid and is selected, with the planned manner of administration in mind, so as to provide for the desired bulk, consistency, etc., when combined with an oligomeric compound conjugate and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzbate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with oligomeric compound conjugates can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of oligomeric compound conjugates may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration that do not deleteriously react with oligomeric compound conjugates can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligomeric compound conjugates of the formulation.

Aqueous suspensions may contain substances that increase the viscosity of the suspension including, for example, sodium carboxymethylcellulose, sorbitol and/or dextran. The suspension may also contain stabilizers.

The compounds of the invention may also be admixed, encapsulated, conjugated or otherwise associated with other molecules, molecule structures or mixtures of compounds, such as, for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Certain embodiments of the invention provide pharmaceutical compositions containing (a) one or more oligomeric compound conjugates and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the oligomeric compound conjugates of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

In another related embodiment, compositions of the invention may contain one or more oligomeric compound conjugates targeted to a first nucleic acid and one or more additional oligomeric compound conjugates targeted to a second nucleic acid target. The two or more combined oligomeric compound conjugates may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The oligomeric compound conjugates of the invention encompass pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes pharmaceutically acceptable salt of an acid form of one of the components of the compositions of the invention. Such salts include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids. Such inorganic acids include, for example, hydrobromic acid, sulfuric acid or phosphoric acid. Such organic acids include, for example, carboxylic, sulfonic, sulfo or phospho acids or N-substituted sulfamic acids, such as, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and amino acids, such as the 20 alpha-amino acids involved in the synthesis of proteins in nature, such as, for example, glutamic acid or aspartic acid, and also phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

Preferred examples of pharmaceutically acceptable salts for oligomeric compound conjugates include, but are not limited to, (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The materials, methods, and examples presented herein are intended to be illustrative, and are not intended to limit the scope of the invention. All publications, patent applications, patents, and other references mentioned herein are incorporated by reference in their entirety. Unless otherwise defined, all technical and scientific terms are intended to have their art-recognized meanings.

The invention can be used in combination with other known agents assisting the cellular uptake to oligonucleotides, or assisting the release of oligonucleotides from endosomes or intracellular compartments into the cytoplasm or cell nuclei by conjugation of those to the oligonucleotide. The known agents can be but is not limited to the following examples; peptides, especially cell penetrating peptides which are known to enhance the cellular uptake of oligonucleotides. Lindsay, M. A. Curr. Opin. Pharmacol., 2002, 2, 587-594. Wadia, J. S. Dowdy, S. F. Curr. Opin. Biotechnol. 2002, 13, 52-56. Gait, M. J. Cell. Mol. Life Sci., 2003, 60, 1-10. lipophilic groups, spermines and polycationic chains. The conjugations can be performed at an internal position at the oligonucleotide or at a terminal postions either the 5'-end or the 3'-end.

Definitions

For the purposes of the previous detailed description of the invention the following definitions are provided for specific terms, which are used in the disclosure of the present invention:

As used herein, the term "metal chelator" is defined as a compound that in solution forms a complex in combination with one or more metal ions. Chelating agents, as used in connection with the present invention, can be defined as compounds that remove metallic ions from solution by forming complexes therewith, with the result that absorption of oligonucleotides through the mucosa is enhanced. Chelating agents of the invention include, but are not limited to, terpyridine (2,2';6',2''-terpyridine), dipyridine, di-(2-picolyl) amine (in single or multiple form linked together), tetrakis (two di-(2-picolyl)amine moieties linked together via x at the N-position), neocuproine (2,9-Dimethyl-1,10-phenanthroline), disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

It contains heteroatoms such as O, S, Se, Si, N or P, in which at least two heteroatoms are bound to the metal. The bonds are covalent or non-covalent.

Examples of chemical structures of preferred metal chelators:

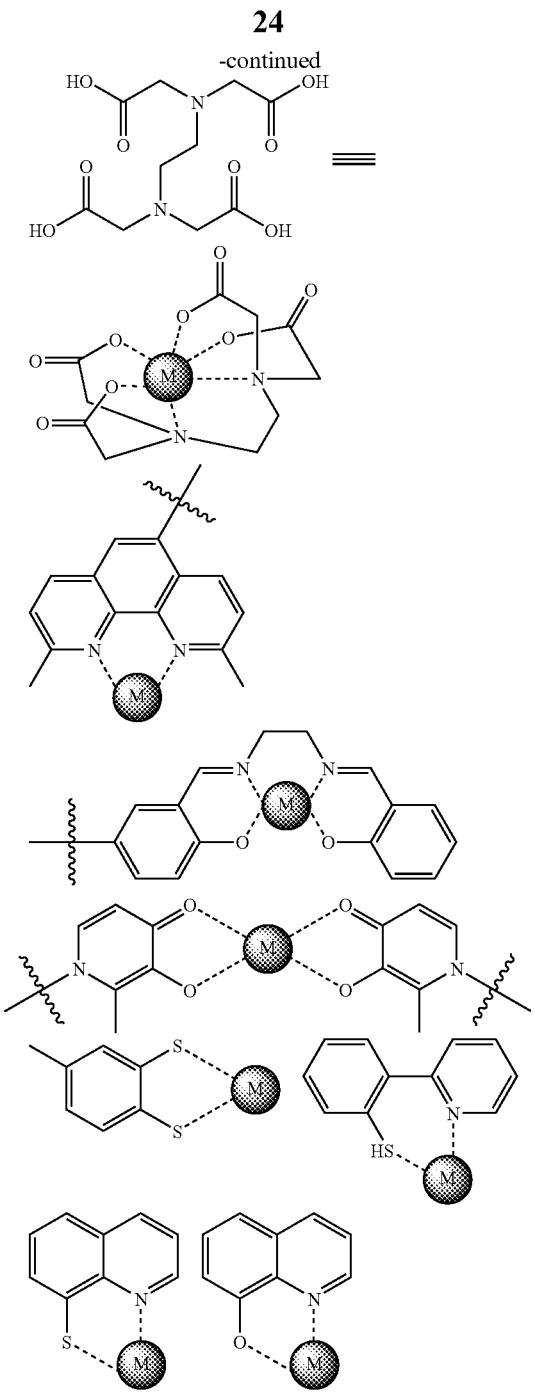

wherein M designates a metal ion.

As used herein, the term "transfection agent" or "transfection reagent" refers to a chemical useful for transfecting cells. "Transfection reagents" provide improved performance for the delivery of DNA, siRNA, oligonucleotides, and RNA, in traditional or difficult-to-transfect cell lines.

As used herein, the term "knock-down" refers to the effect on the expression of a gene, i.e. the altering of the function of a gene so that it can be conditionally expressed.

As used herein, the term "targeting" an oligonucleotide composition of the invention to a particular target nucleic acid means providing the oligonucleotide composition to said target in such a way that the oligonucleotide composition is able to bind to and modulate the function of said target.

The singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

"Sample" refers to a sample of cells, or tissue or fluid isolated from an organism or organisms, including but not limited to, for example, skin, plasma, serum, spinal fluid, lymph fluid, synovial fluid, urine, tears, blood cells, organs, tumours, and also to samples of in vitro cell culture constituents (including but not limited to conditioned medium resulting from the growth of cells in cell culture medium, recombinant cells and cell components).

An "organism" refers to a living entity, including but not limited to, for example, human, mouse, rat, *Drosophila, C. elegans*, yeast, *Arabidopsis thaliana*, maize, rice, zebra fish, primates, domestic animals, etc.

The terms "Detection probes" or "detection probe" or "detection probe sequence" refer to an oligonucleotide, which oligonucleotide comprises a recognition sequence complementary to a RNA or DNA target sequence, which said recognition sequence is substituted with high-affinity nucleotide analogues, e.g. LNA, to increase the sensitivity and specificity of conventional oligonucleotides, such as DNA oligonucleotides, for hybridization to short target sequences, e.g. mature miRNAs, stem-loop precursor miR-NAs, pri-miRNAs, siRNAs or other non-coding RNAs as well as miRNA binding sites in their cognate mRNA targets, mRNAs, mRNA splice variants, RNA-edited mRNAs and antisense RNAs.

The terms "miRNA" and "microRNA" refer to 18-25 nt non-coding RNAs. They are processed from longer (ca 75 nt) hairpin-like precursors termed pre-miRNAs. MicroRNAs assemble in complexes termed miRNPs and recognize their targets by antisense complementarity. If the microRNAs match 100% to their target, i.e. the complementarity is complete, the target mRNA is most probably cleaved, and the miRNA acts like a siRNA. If the match is incomplete, i.e. the complementarity is partial, then the translation of the target mRNA is most probably blocked.

The terms "Small interfering RNAs" or "siRNAs" refer to 21-25 nt RNAs derived from processing of linear double-stranded RNA. siRNAs assemble in complexes termed RISC (RNA-induced silencing complex) and target complementary RNA sequences for endonucleolytic cleavage. Synthetic siR-NAs also recruit RISCs and are capable of cleaving complementary RNA sequences The term "RNA interference" (RNAi) refers to a phenomenon where double-stranded RNA homologous to a target mRNA leads to degradation of the targeted mRNA. More broadly defined as degradation of target mRNAs by fully or partly complementary siRNAs.

The term "piRNA" (Piwi interacting RNAs) referes to small noncoding RNAs of 26-31-nucleotides identified through their interaction with PIWI proteins.

The term "RNAa" (dsRNA-induced gene activation) referes to the mechanism in which small double stranded RNAs of approximately 21 nucleotides, partly of fully complementary to a promoter region of a gene results in upregulation of the gene encoded mRNA.

The term "gene" referes a locatable region of genomic sequence, corresponding to a unit of inheritance, which is associated with regulatory regions, transcribed regions and/or other functional sequence regions.

The term "Recognition sequence" refers to a nucleotide sequence that is complementary to a region within the target nucleotide sequence essential for sequence-specific hybridization between the target nucleotide sequence and the recognition sequence.

The term "functional moiety" as used herein refers to any atom or molecule which can be used to provide a specific functionality and which can be attached to a nucleic acid or protein or to any atom or molecule. Functional moieties may comprise a "label" or a "cell penetration enhancer"

The term "cell penetration enhancer" as used herein refers to any atom or molecule which can be attached to a nucleic acid or protein or to any atom or molecule for the promotion of cell penetration either in itself or due to its ability to improve the effect of a transfection agent or a combination of both.

The term "label" as used herein refers to any atom or molecule which can be used to provide a detectable (preferably quantifiable) signal, either directly or indirectly and which can be attached to a nucleic acid or protein or to any atom or molecule.

Labels may provide signals detectable by fluorescence, radioactivity, colorimetric, X-ray diffraction or absorption, magnetism, enzymatic activity, and the like or may provide recognition sites for labelling reagents such as antibodies or nucleic acids having detectable labels ("indirect labelling"; "indirect detection").

Labels may also comprise ligands. In the present context "ligand" means something, which binds. Ligands comprise biotin and functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulphur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e. functional groups or biomolecules that have a specific affinity for sites on particular proteins, antibodies, poly- and oligosaccharides, and other biomolecules.

Further examples of functional parts of labels are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are DANSYL (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6-tetramethylpiperidine), dinitrophenyl, acridines, coumarins, Cy3 and Cy5 (trademarks for Biological Detection Systems, Inc.), erythrosine, coumaric acid, umbelliferone, Texas red, rhodamine, tetramethyl rhodamine, Rox, 7-nitrobenzo-2-oxa-1-diazole (NBD), pyrene, fluorescein, Europium, Ruthenium, Samarium, and other rare earth metals), radio isotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy). Especially interesting examples are biotin, fluorescein, Texas Red, rhodamine, dinitrophenyl, digoxigenin, Ruthenium, Europium, Cy5, Cy3, etc.

As used herein, the terms "nucleic acid", "polynucleotide" and "oligonucleotide" refer to primers, probes, oligomer fragments to be detected, oligomer controls and unlabelled blocking oligomers and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA. The oligonucleotide is comprised of a sequence of approximately at least 3 nucleotides, preferably at least about 6 nucleotides, and more preferably at least about 8-30 nucleotides corresponding to a region of the designated target nucleotide sequence. "Corresponding" means identical to or complementary to the designated sequence. The oligonucleotide is not necessarily physically derived from any existing or natural sequence but may be generated in any manner, including chemical synthesis, DNA replication, reverse transcription or a combination thereof.

The term "nucleic acid" intend a polynucleotide of genomic DNA or RNA, cDNA, semi synthetic, or synthetic origin which, by virtue of its origin or manipulation. Because mononucleotides are reacted to make oligonucleotides in a manner such that the 5'-OH of one mononucleotide pentose ring is attached to the 3' oxygen of its neighbour in one direction via a phosphodiester linkage, an end of an oligonucleotide is referred to as the "5' end" if its 5'-OH is not linked to the 3' oxygen via a phosphodiester linkage of a mononucleotide pentose ring and as the "3' end" if its 3' oxygen is not linked to a 5'-OH of a subsequent mononucleotide pentose ring. As used herein, a nucleic acid sequence, even if internal to a larger oligonucleotide or having attached free phosphate groups, also may be said to have a 5' and 3' ends. When two different, non-overlapping oligonucleotides anneal to different regions of the same linear complementary nucleic acid sequence, the 3' end of one oligonucleotide points toward the 5' end of the other; the former may be called the "upstream" oligonucleotide and the latter the "downstream" oligonucleotide.

The complement of a nucleic acid sequence as used herein refers to an oligonucleotide which, when aligned with the nucleic acid sequence such that the 5' end of one sequence is paired with the 3' end of the other, is in "antiparallel association." Bases not commonly found in natural nucleic acids may be included in the nucleic acids of the present invention include, for example, inosine and 7-deazaguanine. Complementarity may not be perfect; stable duplexes may contain mismatched base pairs or unmatched bases. Those skilled in the art of nucleic acid technology can estimate duplex stability empirically considering a number of variables including, for example, the length of the oligonucleotide, percent concentration of cytosine and guanine bases in the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the duplexes have disassociated.

The term "nucleobase" covers the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine (also termed "mC"), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, *Nucleic Acid Research,* 25: 4429-4443, 1997. The term "nucleobase" thus includes not only the known purine and pyrimidine heterocycles, but also heterocyclic analogues. tautomers thereof. Further naturally and non naturally occurring nucleobases include those disclosed in U.S. Pat. No. 3,687,808; in chapter 15 by Sanghvi, in *Antisense Research and Application,* Ed. S. T. Crooke and B. Lebleu, CRC Press, 1993; in Englisch, et al., *Angewandte Chemie, International Edition,* 30: 613-722, 1991 (see, especially pages 622 and 623, and in the *Concise Encyclopedia of Polymer Science and Engineering,* J. I. Kroschwitz Ed., John Wiley & Sons, pages 858-859, 1990, Cook, *Anti-Cancer DrugDesign* 6: 585-607, 1991, each of which are hereby incorporated by reference in their entirety).

The term "nucleosidic base" or "nucleobase analogue" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole or a 5-nitroindole. Other preferred compounds include pyrene and pyridyloxazole derivatives, pyrenyl, pyrenylmethylglycerol derivatives and the like. Other preferred universal bases include, pyrrole, diazole or triazole derivatives, including those universal bases known in the art. Further exemplary modified bases are described in Guckian, et al., Journal of the American Chemical Society, 122: 2213-2222, 2000, EP 1 072 679 and WO 97/12896.

By "oligonucleotide," "oligomer," or "oligo" is meant a successive chain of monomers (e.g., glycosides of heterocyclic bases) connected via internucleoside linkages. The linkage between two successive monomers in the oligonucleotide consist of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O, $O^-$)—, —P(O,OH)—, —PO(BH$_3$)—, —P(O,$S^-$)—, —P(O, SH)—, —P(S,$O^-$)—, —P(S,OH)—, P(S,$S^-$)—, —P(S, SH)—, —PO(R")—, —PO(OCH$_3$)—, and —PO($NHR^H$)—, where $R^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—NR$^H$—CH$_2$—, —O—NR$^H$—, —O—CH$_2$—S—, —S—CH$_2$—O—, —CH$_2$—CH$_2$—S—, —O—CH$_2$—CH$_2$—S—, —S—CH$_2$—CH= (including R$^5$ when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NR$^H$—, —NR$^H$—S(O)$_2$—CH$_2$—, —O—S(O)$_2$—CH$_2$—, —O—P(O,OH)—O—, —O—P(O,O$^-$)—O—, —O—P(O,SH)—O—, —O—P(O,S$^-$)—O—, O—P(S,OH)—O—, —O—P(S,O$^-$)—O—, —O—P(S,SH)—O—, —O—P(S,S$^-$)—O—, —S—P(O,OH)—O—, —S—P(O,O$^-$)—O—, —S—P(O,SH)—O—, —S—P(O,S$^-$)—O—, —S—P(S,OH)—O—, —S—P(S,O$^-$)—O—, —S—P(S,S$^-$)—O—, —S—P(S,SH)—O—, —O—P(O,O$^-$)—S—, O—P(O,OH)—S—, —O—P(O,SH)—S—, —O—P(O,S$^-$)—S—, —O—P(S,OH)—S—, —O—P(S,O$^-$)—S—, —O—P(S,SH)—S—, —O—P(S,S$^-$)—S—, —S—P(O,O$^-$)—S—, —S—P(O,OH)—S—, —S—P(O,SH)—S—, —S—P(O,S$^-$)—S—, S—P(S,OH)—S—, —S—P(S,O$^-$)—S—, —S—P(S,SH)—S—, —S—P(S,S$^-$)—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—NR$^H$—, —NR$^H$—P(O,OH)—O—, —O—P(O,NR$^H$)—O—, —CH$_2$—P(O,OH)—O—, —O—P(O,OH)—CH$_2$—, and —O—Si(R")$_2$—O—; among which —CH$_2$—CO—NR$^H$—, —CH$_2$—NR$^H$—O—, —S—CH$_2$—O—, —O—P(O,OH)—O—, —O—P(O,SH)—O—, —O—P(S,SH)—O—, —NR$^H$—P(O,OH)—O—, —O—P(O,NR$^H$)—O—, —O—PO(R")—O—, —O—PO(CH$_3$)—O—, and —O—PO(NHR$^N$)—O—, where R$^H$ is selected form hydrogen and C$_{1-4}$-alkyl, and R" is selected from C$_{1-6}$-alkyl and phenyl, are especially desirable. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443. The left-hand side of the internucleoside linkage is bound to the 5-membered ring at the 3'-position, whereas the right-hand side is bound to the 5'-position of a preceding monomer.

By "LNA" or "LNA monomer" (e.g., an LNA nucleoside or LNA nucleotide) or an LNA oligomer (e.g., an oligonucleotide or nucleic acid) is meant a nucleoside or nucleotide analogue that includes at least one LNA monomer. LNA monomers as disclosed in PCT Publication WO 99/14226 are in general particularly desirable modified nucleic acids for incorporation into an oligonucleotide of the invention. Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc. Desirable LNA monomers and their method of synthesis also are disclosed in U.S. Pat. No. 6,043,060, U.S. Pat. No. 6,268,490, PCT Publications WO 01/07455, WO 01/00641, WO 98/39352, WO 00/56746, WO 00/56748 and WO 00/66604 as well as in the following papers: Morita et al., Bioorg. Med. Chem. Lett. 12(1):73-76, 2002; Hakansson et al., Bioorg. Med. Chem. Lett. 11(7):935-938, 2001; Koshkin et al., J. Org. Chem. 66(25):8504-8512, 2001; Kvaerno et al., J. Org. Chem. 66(16):5498-5503, 2001; Hakansson et al., J. Org. Chem. 65(17):5161-5166, 2000; Kvaerno et al., J. Org. Chem. 65(17):5167-5176, 2000; Pfundheller et al., Nucleosides Nucleotides 18(9):2017-2030, 1999; and Kumar et al., Bioorg. Med. Chem. Lett. 8(16):2219-2222, 1998.

When at least two LNA nucleotides are included in the oligonucleotide composition, these may be consecutive or separated by one or more non-LNA nucleotides. In one aspect, LNA nucleotides are alpha-L-LNA and/or xylo LNA nucleotides as disclosed in PCT Publications No. WO 2000/66604 and WO 2000/56748.

Preferred LNA monomers, also referred to as "oxy-LNA" are LNA monomers which include bicyclic compounds as disclosed in PCT Publication WO 03/020739 wherein the bridge between R$^{4'}$ and R$^{2'}$ together designate —CH$_2$—O— or —CH$_2$—CH$_2$—O—.

Preferred LNA monomers, also referred to as "amino-LNA" are LNA monomers which include bicyclic compounds as claimed in U.S. Pat. No. 6,794,499 og U.S. Pat. No. 6,670,461 as well as disclosed in the following papers: Singh et al, J.Org.Chem. 1998, 63, 6078-9, Singh et al, J.Org.Chem. 1998, 63, 10035-9 and Rosenbohm et al, Org. Biomol. Chem., 2003, 1, 655-663.

Exemplary 5', 3', and/or 2' terminal groups include —H, —OH, halo (e.g., chloro, fluoro, iodo, or bromo), optionally substituted aryl, (e.g., phenyl or benzyl), alkyl (e.g., methyl or ethyl), alkoxy (e.g., methoxy), acyl (e.g. acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethoxytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

It is understood that references herein to a nucleic acid unit, nucleic acid residue, LNA monomer, or similar term are inclusive of both individual nucleoside units and nucleotide units and nucleoside units and nucleotide units within an oligonucleotide.

The term "chemical moiety" refers to a part of a molecule. "Modified by a chemical moiety" thus refer to a modification of the standard molecular structure by inclusion of an unusual chemical structure. The attachment of said structure can be covalent or non-covalent.

The term "inclusion of a chemical moiety" in an oligonucleotide probe thus refers to attachment of a molecular structure. Such as chemical moiety include but are not limited to covalently and/or non-covalently bound minor groove binders (MGB) and/or intercalating nucleic acids (INA) selected from a group consisting of asymmetric cyanine dyes, DAPI, SYBR Green I, SYBR Green II, SYBR Gold, PicoGreen, thiazole orange, Hoechst 33342, Ethidium Bromide, 1-O-(1-pyrenylmethyl)glycerol and Hoechst 33258. Other chemical moieties include the modified nucleobases, nucleosidic bases or LNA modified oligonucleotides.

"High affinity nucleotide analogue" or "affinity-enhancing nucleotide analogue" refers to a non-naturally occurring nucleotide analogue that increases the "binding affinity" of an oligonucleotide probe to its complementary recognition sequence when substituted with at least one such high-affinity nucleotide analogue. Preferred analogues are LNA and PNA (peptide nucleid acid).

As used herein, a probe with an increased "binding affinity" for a recognition sequence compared to a probe which comprises the same sequence but does not comprise a stabilizing nucleotide, refers to a probe for which the association constant ($K_a$) of the probe recognition segment is higher than the association constant of the complementary strands of a double-stranded molecule. In another preferred embodiment, the association constant of the probe recognition segment is higher than the dissociation constant ($K_d$) of the complementary strand of the recognition sequence in the target sequence in a double stranded molecule.

Monomers are referred to as being "complementary" if they contain nucleobases that can form hydrogen bonds according to Watson-Crick base-pairing rules (e.g. G with C, A with T or A with U) or other hydrogen bonding motifs such as for example diaminopurine with T, 5-methyl C with G, 2-thiothymidine with A, inosine with C, pseudoisocytosine with G, etc.

The term "succeeding monomer" relates to the neighbouring monomer in the 5'-terminal direction and the "preceding monomer" relates to the neighbouring monomer in the 3'-terminal direction.

The term "target nucleic acid" or "target ribonucleic acid" refers to any relevant nucleic acid of a single specific sequence, e.g., a biological nucleic acid, e.g., derived from a patient, an animal (a human or non-human animal), a plant, a bacteria, a fungi, an archae, a cell, a tissue, an organism, etc. For example, where the target ribonucleic acid or nucleic acid is derived from a bacteria, archae, plant, non-human animal, cell, fungi, or non-human organism, the method optionally further comprises selecting the bacteria, archae, plant, non-human animal, cell, fungi, or non-human organism based upon detection of the target nucleic acid. In one embodiment, the target nucleic acid is derived from a patient, e.g., a human patient. In this embodiment, the invention optionally further includes selecting a treatment, diagnosing a disease, or diagnosing a genetic predisposition to a disease, based upon detection of the target nucleic acid.

"Target sequence" refers to a specific nucleic acid sequence within any target nucleic acid.

The term "stringent conditions", as used herein, is the "stringency" which occurs within a range from about $T_m$-5° C. (5° C. below the melting temperature ($T_m$) of the probe) to about 20° C. to 25° C. below $T_m$. As will be understood by those skilled in the art, the stringency of hybridization may be altered in order to identify or detect identical or related polynucleotide sequences. Hybridization techniques are generally described in *Nucleic Acid Hybridization, A Practical Approach*, Ed. Hames, B. D. and Higgins, S. I., IRL Press, 1985; Gall and Pardue, Proc. Nat. Acad. Sci., USA 63: 378-383, 1969; and John, et al. *Nature* 223: 582-587, 1969.

The term "intracellular avalibility" refers to intracellular probes, which are not entrapped in endosomes or other compartmens and thereby free to hybridize with their targets found in cytoplasma and nucleus.

EXAMPLES

The invention will now be further illustrated with reference to the following examples. It will be appreciated that what follows is by way of example only and that modifications to detail may be made while still falling within the scope of the invention.

Example 1

Synthesis of 4'-hexanoic acid-2,2':6',2"-terpyridine

Scheme 1. Synthesis of 4'-hexanoic acid-2,2':6',2"-terpyridine

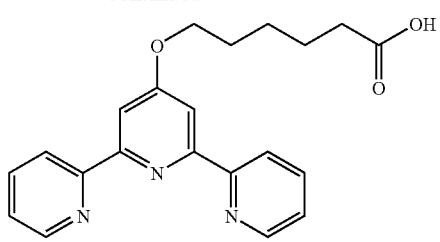

-continued

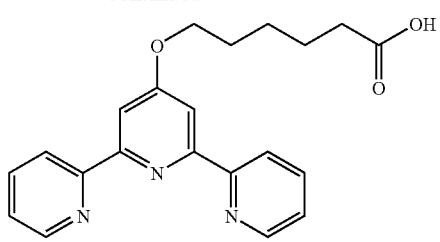

The synthesis was carried out according to litt. [P. R. Andres, R. Lunkwitz, G. R. Pabst, K. Böhn, D. Wouters, S. Schmatloch, U. S. Schuberth, *Eur. J. Org.Chem.* 2003, 19, 3769-3776]

The oligomers and LNA substituted oligomers were chemically synthesized using commercially available methods and equipment as described in the art (Koshkin et al., *Tetrahedron* 54: 3607-30, 1998). For example, the solid phase phosphoramidite method can be used to produce short LNA probes (Caruthers, et al., *Cold Spring Harbor Symp. Quant. Biol.* 47:411-418, 1982, Adams, et al., *J. Am. Chem. Soc.* 105: 661 (1983).

The amino $C_6$-linker was coupled to the 5'-end using the solid phase phospramidite approach having the amino group protected with a monomethoxytrityl (MMT) group (commercially available from Glenn research, 10-1906-02). The MMT-group was removed using a final deblocking step on the synthesizer. The oligonucleotide (synthesized on a 0.2 μmol scale) was subjected to a solution (0.3 mL) of 4'-hexanoic acid-2,2':6',2"-terpyridine (20 mg, 55 mmol), (benzotriazol-1-yloxy)tris(dimethylamino)phosphonium hexafluorophosphate (BOP) (22 mg, 50 mmol) diisopropylethylamine (DIPEA) (10 μL, 57 mmol) in DMF (1 mL) in a vial. The resin containing the oligonucleotide was vortexed gently for 45 min. The solution was aspired using a syringe. The resin was subsequently washed with DMF (2×1 mL) and $CH_3CN$ (2×1 mL). The oligonucleotide was deprotected with ammonia treatment using standard conditions and subsequently purified by RP-HPLC (Scheme 2).

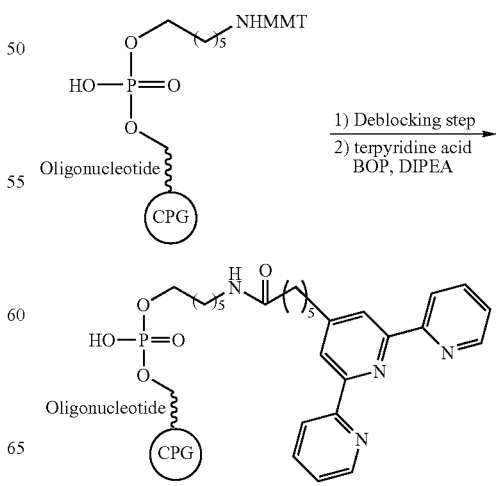

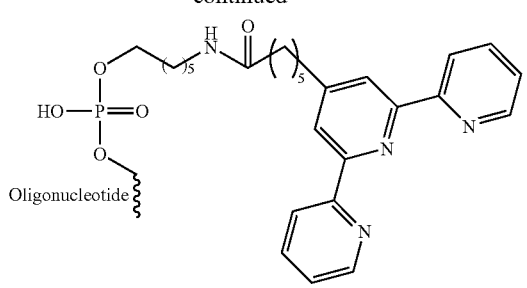

A number of LNA miRNA knockdown oligonucleotides were synthesized and tested in cell culture for their ability to knockdown an endogenous miRNA. For these experiments we used a dual reporter system in which a reporter plasmid containing the firefly reporter gene and a miRNA target sequence was co-transfected with a normalization vector (Renilla). To estimate the potency of miRNA knockdown oligonucleotides the luminescence signal of the miRNA firefly reporter plasmid was compared to the parental firefly reporter plasmid deprived of the miRNA target site. After leaving the cells for 3-5 h with plasmids and transfection reagents, the cells were washed twice in media and the oligonucleotides were added at the indicated concentrations. 24 h post plasmid transfection the plates were analyzed using the Dual-luciferase system (Promega).

Example 2

Oligo Nucleotide Synthesis

TABLE 2

Oligonucleotide and sequences are used in the experiments:

| Oligonucleotide name | Oligonucleotide sequence |
|---|---|
| AntimiR-21-oligo-nucleotide A | TmCagTctGatAagmCTa (SEQ ID NO: 4) |
| AntimiR-21-oligo-nucleotide B | tmCaamCatmCagTctGatAagmCta (SEQ ID NO: 5) |
| AntimiR-21-oligo-nucleotide C | TmCagTcTgaTAAGmCTa (SEQ ID NO: 6) |
| AntimiR-21-oligo-nucleotide A-Terpyr | Terpyr-TmCagTctGatAagmCTa (SEQ ID NO: 7) |
| AntimiR-21-oligo-nucleotide B-Terpyr | Terpyr-tmCaamCatmCagTctGatAagmCta (SEQ ID NO: 2) |
| AntimiR-21-oligo-nucleotide C-Terpyr | Terpyr-TmCagTcTgaTAACmCTa (SEQ ID NO: 8) |
| AntimiR-21-oligo-nucleotide B-Terpyr-CPP | Terpyr-tmCaamCatmCagTctGatAagmCta-CPP (SEQ ID NO: 9) |
| AntimiR-21-oligo-nucleotide C-Terpyr-CPP | Terpyr-TmCagTcTgaTAAGmCTa-CPP (SEQ ID NO: 10) |
| Negative | gTgtAacAcgTctAtamCgcmCca (SEQ ID NO: 11) |

TABLE 2-continued

Oligonucleotide and sequences are used in the experiments:

| Oligonucleotide name | Oligonucleotide sequence |
|---|---|
| Negative-Terpyr | Terpyr-gTgtAacAcgTctAtamCgcmCca (SEQ ID NO: 12) |

Capital G, A, T or mC denote LNA monomers, mC denotes 5-methyl cytosine, Terpyr denotes terpyridine, CPP denotes Cell Penetrating Peptide.

a) Conjugating Cell Penetrating Peptides (CPP) to Oligonucleotides

The CPP was attached at the 3'-ends of the oligonucleotides via disulphide linkage. This was accomplished by introducing a thiol group at the 3'-ends of the oligonucleotidse and coupled this with a CPP using a kit provided by Cambrex (Transport™ Protein Delivery Reagent, 50568). The oligonucleotide was synthesized on a 1-O-Dimethoxytrityl-propyl-disulfide, 1'-succinyl-lcaa-CPG (Glenn Research, 20-2933-42) using standard procedure for LNA oligonucleotides (Exiqon website) The amino-C6-linker (6-(4-Monomethoxytritylamino)hexyl-(2-cyanoethyl)-(N,N-di-isopropyl)-phosphoramidite, Glenn Research, 10-1906-02) was introduced at the 5'-end and terpyiridine was introduced as previously described. The oligonucleotides were deprotected using saturated aqueous ammonia at 55° C. for 6 h. and subsequently HPLC purified. Just prior to the conjugation with CPP the disulphide bridge was cleaved using DTT pH 8.5 for 16 h and subsequently desalted on a NAP-10 columns (GE Health Care, 17-0854-01). The conjugation with CPP was performed as described in the procedure provided by (Cambrex). The products were verified by MALDI-MS.

b) miRNA Reporter Constructs

The pMIR-21 was constructed by inserting a miR-21 complementary sequence in the 3'UTR of the pMIR-REPORT (Ambion) containing the firefly luciferase reporter gene. In short this was done by annealing oligonucleotide I (A: 5'-AAT GCA CTA GTT CAA CAT CAG TCT GAT AAG CTA GCT CAG CAA GCT TAA TGC- 3'; SEQ ID NO: 13) and II (B: 5'-GCA TTA AGC TTG CTG AGC TAG CTT ATC AGA CTG ATG TTG AAC TAG TGC ATT-3'; SEQ ID NO: 14). This fragment and the pMIR-REPORT vector were then digested with SpeI and HindIII and the fragment was subsequently cloned into the SpeI and HindIII sites of pMIR-REPORT vector using standard techniques, thereby generating pMIR-21.

c) Reporter Assays

HeLa and HeLa 3S cells were propagated in Dulbecco's Modified Eagle's Minimal Essential Medium (DMEM) with Glutamax™ (Invitrogen) and supplemented with 10% foetal bovine serum (FBS). On the day prior to transfection cells were seeded in 96-well plates (Corning) at a density of 7000 cells/well. Cells were transfected using Xtreme Gene siRNA (Roche), with 70 ng/well of pMIR-21 reporter and 30 ng/well of the pGL4.73 Renilla (Promega) reporter plasmid for normalisation. When indicated transfection mix also contained oligonucleotides resulting in a final concentration of 5-100 nM.

After 3-4 h, media with transfection mix was removed and cells were washed four times in PBS and supplemented with fresh media. Subsequently, oligonucleotides were added directly to the media resulting in final concentrations of 25-1000 nM. Luciferase activities (Firefly and Renilla) were measured 24 h later using the Dual Glow Luciferase kit (Promega) on a BMG Optima luminometer.

For the MCF7 cells, experiments were carried out as above, however these cells were propagated in Roswell Park Memorial Institute medium (RPMI) 1640 with Glutamax™ (Invitrogen) and supplemented with 10% FBS. Cells were seeded to 15000 cell/well on the day prior to transfection and left for 48 h before measuring luciferase activity. After luminescence measurements relative light units (RLU) were corrected for background and firefly luminescence (FL) was normalised to Renilla luminescence (RL). Data presented in the diagram shows "fold up regulation" of the normalised (FL/RL) signal of the microRNA reporter vector relative to the no oligonucleotide control.

Example 3

Terpyridine Conjugated Oligonucleotides Enhance miRNA Knockdown Potency when Transfected To measure the effect of microRNA inhibiting oligonucleotides a luciferase based miR-21 sensor reporter was constructed. This reporter harbours a sequence fully complementary to hsa-miR-21. When the reporter mRNA is recognized by a miR-21 containing RISC complex, the luciferase encoding mRNA is cleaved and subsequently degraded. The luciferase expression level thereby reflects the endogenous level of active miR-21.

A wide variety of cell lines are known to express miR-21 at high levels and miR-21 was therefore chosen for the initial experiments. In one line of experiments reporter plasmid, pMIR-21, and miR-21 inhibiting oligonucleotides were co-transfected (see materials and methods).

Reporter data show that when co-transfected with plasmid all oligonucleotides both conjugated to terpyridine and unconjugated were functional in inhibiting endogenous miR-21 as shown by the 5-15 fold increase in expression of the miR-21 sensor reporter (FIG. 1). Moreover, terpyridine conjugated oligonucleotides showed slightly enhanced potency in particular at 5 and 20 nM oligonucleotide concentration.

Example 4

Terpyridine Conjugated Oligonucleotides Strongly Increase Knockdown Potency of Oligonucleotides in Absence of Transfection Reagent To investigate the effect of terpyridine in absence of transfection reagent, cells were transfected with reporter plasmids, washed thoroughly and subsequently incubated with oligonucleotides diluted directly in growth media (see materials and methods). These data (FIG. 2) show that terpyridine conjugated oligonucleotides in absence of transfection reagents are capable of inhibiting miR-21, resulting in a 7-8 fold up regulation of the miR-21 reporter plasmid at a final oligonucleotide concentration of 160 nM.

Unconjugated oligonucleotides produced only a limited up regulation of the miR-21 reporter and only at high oligonucleotide concentrations.

Example 5

Terpyridine Conjugated Oligonucleotides are Functional in Several Cell Lines

HeLa cells are known to be relatively easy to transfect and may therefore also facilitate cellular uptake of terpyridine conjugated oligonucleotides to a much higher degree than more difficult to transfect cell lines. To investigate if terpyridine mediated delivery also applies to harder-to-transfect cell lines a similar reporter experiment were carried out in MCF7 cells. HeLa and HeLa 3S cells were also included in this experiment.

Reporter results (FIG. 3) demonstrate that terpyridine conjugated oligonucleotides indeed are capable of mediating an inhibitory effect on miR-21 in both HeLa, HeLa 3S and MCF7 as shown by the approximately 6-10 fold up regulation of the reporter compared to the no oligo-control. None of the unconjugated control oligonucleotides were capable of up regulating the miR-21 reporter significantly.

In conclusion terpyridine conjugated to miR-21-inhibiting LNA-oligonucleotides mediate specific inhibitions of endogenous miR-21 in both easy and hard-to-transfect cell lines in absence of transfection reagents.

Example 6

Knockdown Experiments with Terpyridine Modified Oligonucleotides and Cell Penetrating Peptide (CPP)

Presently it is unclear at which step in functional oligonucleotide delivery that terpyridine acts, however, the above data shows a clear positive effect on knockdown potency of terpyridine conjugation both when transfected and when delivered without transfection reagent. The strong knockdown potency shown when transfected indicates that cellular uptake may be a limiting parameter for knockdown potency of terpyridine oligonucleotides in absence of transfection reagents.

It is thus of interest, whether terpyridine could also enhance knockdown potency when delivered with other cellular delivery agents, such as a cell penetrating peptide (CPP). To investigate this a number of terpyridine-CPP conjugated oligonucleotides were generated (see materials and methods) and tested in the established pMIR-21 reporter system in absence of transfection reagents as described above.

The results (FIG. 4) show that in all cases terpyridine in combination with CPP increased functional delivery of the oligonucleotides as indicated by an increase in knock down potency of the double conjugated oligonucleotides. The increase was subtle.

These data demonstrate that the attachment-of metal chelators, in particular terpyridine, can act in synergy with other functional groups to enhance cellular delivery of oligonucleotides.

The invention claimed is:

1. A compound of formula I:

OLIGO-L-CHEL (I)

wherein "OLIGO" designates an oligonucleotide composition containing one or two LNA monomers within each three nucleotide segment, "CHEL" is 2,2':6',2"-terpyridine, and "L" is a linking moiety.

2. A compound of claim 1 wherein "L" is produced from 6-(4-Monomethoxytritylamino)hexyl-(2-cyanoethyl)-(N,N-diisopropyl)-phosphoramidite.

3. A compound of claim 1 wherein the metal chelator is able to remove free metallic ions from solution by forming complexes.

4. A compound of claim 1 wherein at least one LNA monomer is selected from oxy-LNA or amino-LNA.

5. A compound of claim 1 further comprising one or more labels.

6. A method of synthesizing a compound of formula I

OLIGO-L-CHEL (I)

wherein "OLIGO" designates an oligonucleotide composition containing an LNA monomer at every third nucleotide, "CHEL" is 2,2':6',2"-terpyridine, and "L" is a linking moiety, comprising the following steps:

a) coupling said linking moiety with a suitable solid phase protecting group to the 5'-end of an oligonucleotide composition attached to a solid phase at the 3' end,
b) cleaving off said solid phase protecting group using a suitable reagent,
c) conjugating to said linking moiety 2,2':6',2"-terpyridine, and
d) deprotecting said 3' end.

7. A method of synthesizing a compound of formula I

OLIGO-L-CHEL (I)

wherein "OLIGO" designates an oligonucleotide composition containing one or two LNA monomers within each three nucleotide segment, "CHEL" is 2,2':6',2"-terpyridine, and "L" is a linking moiety, comprising the following steps:

a) attaching said linking moiety to a solid phase, b) synthesizing an oligonucleotide composition comprising said linking moiety, c) deprotecting said oligonucleotide composition from said solid phase, and d) conjugating to said linking moiety 2,2':6',2"-terpyridine.

8. A kit comprising a compound of formula I

OLIGO-L-CHEL (I)

wherein "OLIGO" designates an oligonucleotide composition containing one or two LNA monomers within each three nucleotide segment, "CHEL" is 2,2':6',2"-terpyridine, and "L" is a linking moiety for use in diagnostics.

9. A method of synthesizing a compound of formula I

OLIGO-L-CHEL                                    (I)

wherein "OLIGO" designates an oligonucleotide composition containing one or two LNA monomers within each three nucleotide segment, "CHEL" is 2,2':6,2"-terpyridine, and "L" is a linking moiety, comprising the following steps:

a) coupling said linking moiety with a suitable solid phase protecting group to the 5-end of an oligonucleotide composition attached to a solid phase at the 3' end,
b) cleaving off said solid phase protecting group using a suitable reagent,
c) conjugating to said linking moiety 2,2':6',2"-terpyridine, and
d) deprotecting said 3' end.

10. A compound of claim 1 with an antisense, silencing or knock-down efficacy.

* * * * *

SEQUENCE LISTING

<160> NUMBER OF SEQ ID NOS: 14

<210> SEQ ID NO 1
<211> LENGTH: 21
<212> TYPE: RNA
<213> ORGANISM: Artificial Sequence
<220> FEATURE:
<223> OTHER INFORMATION: Synthetic Construct -continued

<400> SEQUENCE: 1
uagcuuauca gacugaugug a                                      21

<210> SEQ ID NO 2
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Modified by terpyridine
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid 5-methylcytosine
<220> FEATURE:
<221> NAME/KEY: misc_feature
<222> LOCATION: (8)..(8)
<223> OTHER INFORMATION: n = locked nucleic acid 5-methylcytosine
<220> FEATURE:
<221> NAME/KEY: misc_feature
<222> LOCATION: (11)..(11)
<223> OTHER INFORMATION: n = locked nucleic acid thymine
<220> FEATURE:
<221> NAME/KEY: misc_feature
<222> LOCATION: (14)..(14)
<223> OTHER INFORMATION: n = locked nucleic acid guanine
<220> FEATURE:
<221> NAME/KEY: misc_feature
<222> LOCATION: (17)..(17)
<223> OTHER INFORMATION: n = locked nucleic acid adenine
<220> FEATURE:
<221> NAME/KEY: misc_feature
<222> LOCATION: (20)..(20)
<223> OTHER INFORMATION: n = locked nucleic acid 5-methylcytosine

<400> SEQUENCE: 2
tnaanatnag nctnatnagn ta                                     22

<210> SEQ ID NO 3
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n = locked nucleic acid thymine
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid 5-methylcytosine
<220> FEATURE:
<221> NAME/KEY: misc_feature
<222> LOCATION: (8)..(8)
<223> OTHER INFORMATION: n = locked nucleic acid 5-methylcytosine
<220> FEATURE:
<221> NAME/KEY: misc_feature
<222> LOCATION: (11)..(11)
<223> OTHER INFORMATION: n = locked nucleic acid thymine
<220> FEATURE:
<221> NAME/KEY: misc_feature
<222> LOCATION: (14)..(14)
<223> OTHER INFORMATION: n = locked nucleic acid guanine

```
<220> FEATURE:
<221> NAME/KEY: misc_feature
<222> LOCATION: (17)..(17)
<223> OTHER INFORMATION: n = locked nucleic acid adenine
<220> FEATURE:
<221> NAME/KEY: misc_feature
<222> LOCATION: (20)..(20)
<223> OTHER INFORMATION: n = locked nucleic acid 5-methylcytosine

<400> SEQUENCE: 3
nnaanatnag nctnatnagn ta                                              22

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n = locked nucleic acid thymine
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid thymine
<220> FEATURE:
<221> NAME/KEY: misc_feature
<222> LOCATION: (8)..(8)
<223> OTHER INFORMATION: n = locked nucleic acid guanine
<220> FEATURE:
<221> NAME/KEY: misc_feature
<222> LOCATION: (11)..(11)
<223> OTHER INFORMATION: n = locked nucleic acid adenine
<220> FEATURE:
<221> NAME/KEY: misc_feature
<222> LOCATION: (14)..(14)
<223> OTHER INFORMATION: n = locked nucleic acid 5-methylcytosine
<220> FEATURE:
<221> NAME/KEY: misc_feature
<222> LOCATION: (15)..(15)
<223> OTHER INFORMATION: n = locked nucleic acid thymine

<400> SEQUENCE: 4
nnagnctnat nagnna                                                     16

<210> SEQ ID NO 5
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid 5-methylcytosine
<220> FEATURE:
<221> NAME/KEY: misc_feature
<222> LOCATION: (8)..(8)
<223> OTHER INFORMATION: n = locked nucleic acid 5-methylcytosine
<220> FEATURE:
<221> NAME/KEY: misc_feature
<222> LOCATION: (11)..(11)
<223> OTHER INFORMATION: n = locked nucleic acid thymine
<220> FEATURE:
<221> NAME/KEY: misc_feature
<222> LOCATION: (14)..(14)
<223> OTHER INFORMATION: n = locked nucleic acid guanine
```

```
<220> FEATURE:
<221> NAME/KEY: misc_feature
<222> LOCATION: (17)..(17)
<223> OTHER INFORMATION: n = locked nucleic acid adenine
<220> FEATURE:
<221> NAME/KEY: misc_feature
<222> LOCATION: (20)..(20)
<223> OTHER INFORMATION: n = locked nucleic acid 5-methylcytosine

<400> SEQUENCE: 5
tnaanatnag nctnatnagn ta                                              22

<210> SEQ ID NO 6
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n = locked nucleic acid thymine
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid thymine
<220> FEATURE:
<221> NAME/KEY: misc_feature
<222> LOCATION: (7)..(7)
<223> OTHER INFORMATION: n = locked nucleic acid thymine
<220> FEATURE:
<221> NAME/KEY: misc_feature
<222> LOCATION: (10)..(10)
<223> OTHER INFORMATION: n = locked nucleic acid thymine
<220> FEATURE:
<221> NAME/KEY: misc_feature
<222> LOCATION: (11)..(12)
<223> OTHER INFORMATION: n = locked nucleic acid adenine
<220> FEATURE:
<221> NAME/KEY: misc_feature
<222> LOCATION: (13)..(13)
<223> OTHER INFORMATION: n = locked nucleic acid guanine
<220> FEATURE:
<221> NAME/KEY: misc_feature
<222> LOCATION: (14)..(14)
<223> OTHER INFORMATION: n = locked nucleic acid 5-methylcytosine
<220> FEATURE:
<221> NAME/KEY: misc_feature
<222> LOCATION: (15)..(15)
<223> OTHER INFORMATION: n = locked nucleic acid thymine

<400> SEQUENCE: 6
nnagncngan nnnnna                                                     16

<210> SEQ ID NO 7
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n = locked nucleic acid thymine modified by
      terpyridine
<220> FEATURE:
<221> NAME/KEY: misc_feature
<222> LOCATION: (2)..(2)
<223> OTHER INFORMATION: n = locked nucleic acid 5-methylcytosine
```

```
<220> FEATURE:
<221> NAME/KEY: misc_feature
<222> LOCATION: (5)..(5)
<223> OTHER INFORMATION: n = locked nucleic acid thymine
<220> FEATURE:
<221> NAME/KEY: misc_feature
<222> LOCATION: (8)..(8)
<223> OTHER INFORMATION: n = locked nucleic acid guanine
<220> FEATURE:
<221> NAME/KEY: misc_feature
<222> LOCATION: (11)..(11)
<223> OTHER INFORMATION: n = locked nucleic acid adenine
<220> FEATURE:
<221> NAME/KEY: misc_feature
<222> LOCATION: (14)..(14)
<223> OTHER INFORMATION: n = locked nucleic acid 5-methylcytosine
<220> FEATURE:
<221> NAME/KEY: misc_feature
<222> LOCATION: (15)..(15)
<223> OTHER INFORMATION: n = locked nucleic acid thymine

<400> SEQUENCE: 7
nnagnctnat nagnna                                                  16

<210> SEQ ID NO 8
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n = locked nucleic acid thymine modified by
      terpyridine
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid thymine
<220> FEATURE:
<221> NAME/KEY: misc_feature
<222> LOCATION: (7)..(7)
<223> OTHER INFORMATION: n = locked nucleic acid thymine
<220> FEATURE:
<221> NAME/KEY: misc_feature
<222> LOCATION: (10)..(10)
<223> OTHER INFORMATION: n = locked nucleic acid thymine
<220> FEATURE:
<221> NAME/KEY: misc_feature
<222> LOCATION: (11)..(12)
<223> OTHER INFORMATION: n = locked nucleic acid adenine
<220> FEATURE:
<221> NAME/KEY: misc_feature
<222> LOCATION: (13)..(13)
<223> OTHER INFORMATION: n = locked nucleic acid guanine
<220> FEATURE:
<221> NAME/KEY: misc_feature
<222> LOCATION: (14)..(14)
<223> OTHER INFORMATION: n = locked nucleic acid 5-methylcytosine
<220> FEATURE:
<221> NAME/KEY: misc_feature
<222> LOCATION: (15)..(15)
<223> OTHER INFORMATION: n = locked nucleic acid thymine

<400> SEQUENCE: 8
nnagncngan nnnnna                                                  16

<210> SEQ ID NO 9
<211> LENGTH: 22
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Modified by terpyridine
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid 5-methylcytosine
<220> FEATURE:
<221> NAME/KEY: misc_feature
<222> LOCATION: (8)..(8)
<223> OTHER INFORMATION: n = locked nucleic acid 5-methylcytosine
<220> FEATURE:
<221> NAME/KEY: misc_feature
<222> LOCATION: (11)..(11)
<223> OTHER INFORMATION: n = locked nucleic acid thymine
<220> FEATURE:
<221> NAME/KEY: misc_feature
<222> LOCATION: (14)..(14)
<223> OTHER INFORMATION: n = locked nucleic acid guanine
<220> FEATURE:
<221> NAME/KEY: misc_feature
<222> LOCATION: (17)..(17)
<223> OTHER INFORMATION: n = locked nucleic acid adenine
<220> FEATURE:
<221> NAME/KEY: misc_feature
<222> LOCATION: (20)..(20)
<223> OTHER INFORMATION: n = locked nucleic acid 5-methylcytosine
<220> FEATURE:
<221> NAME/KEY: misc_feature
<222> LOCATION: (22)..(22)
<223> OTHER INFORMATION: Modified by a conjugating cell penetrating
      peptide

<400> SEQUENCE: 9
tnaanatnag nctnatnagn ta                                             22

<210> SEQ ID NO 10
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n = locked nucleic acid thymine modified by
      terpyridine
<220> FEATURE:
<221> NAME/KEY: misc_feature
<222> LOCATION: (2)..(2)
<223> OTHER INFORMATION: n = locked nucleic acid 5-methylcytosine
<220> FEATURE:
<221> NAME/KEY: misc_feature
<222> LOCATION: (5)..(5)
<223> OTHER INFORMATION: n = locked nucleic acid thymine
<220> FEATURE:
<221> NAME/KEY: misc_feature
<222> LOCATION: (7)..(7)
<223> OTHER INFORMATION: n = locked nucleic acid thymine
<220> FEATURE:
<221> NAME/KEY: misc_feature
<222> LOCATION: (10)..(10)
<223> OTHER INFORMATION: n = locked nucleic acid thymine
<220> FEATURE:
<221> NAME/KEY: misc_feature
<222> LOCATION: (11)..(12)
<223> OTHER INFORMATION: n = locked nucleic acid adenine
<220> FEATURE:
<221> NAME/KEY: misc_feature
<222> LOCATION: (13)..(13)
<223> OTHER INFORMATION: n = locked nucleic acid guanine
```

```
<220> FEATURE:
<221> NAME/KEY: misc_feature
<222> LOCATION: (14)..(14)
<223> OTHER INFORMATION: n = locked nucleic acid 5-methylcytosine
<220> FEATURE:
<221> NAME/KEY: misc_feature
<222> LOCATION: (15)..(15)
<223> OTHER INFORMATION: n = locked nucleic acid thymine
<220> FEATURE:
<221> NAME/KEY: misc_feature
<222> LOCATION: (16)..(16)
<223> OTHER INFORMATION: Modified by a conjugating cell penetrating
     peptide

<400> SEQUENCE: 10
nnagncngan nnnnna                                                        16

<210> SEQ ID NO 11
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: n = locked nucleic acid thymine
<220> FEATURE:
<221> NAME/KEY: misc_feature
<222> LOCATION: (5)..(5)
<223> OTHER INFORMATION: n = locked nucleic acid adenine
<220> FEATURE:
<221> NAME/KEY: misc_feature
<222> LOCATION: (8)..(8)
<223> OTHER INFORMATION: n = locked nucleic acid adenine
<220> FEATURE:
<221> NAME/KEY: misc_feature
<222> LOCATION: (11)..(11)
<223> OTHER INFORMATION: n = locked nucleic acid thymine
<220> FEATURE:
<221> NAME/KEY: misc_feature
<222> LOCATION: (14)..(14)
<223> OTHER INFORMATION: n = locked nucleic acid adenine
<220> FEATURE:
<221> NAME/KEY: misc_feature
<222> LOCATION: (17)..(17)
<223> OTHER INFORMATION: n = locked nucleic acid 5-methylcytosine
<220> FEATURE:
<221> NAME/KEY: misc_feature
<222> LOCATION: (20)..(20)
<223> OTHER INFORMATION: n = locked nucleic acid 5-methylcytosine

<400> SEQUENCE: 11
gngtnacncg nctntangcn ca                                                 22

<210> SEQ ID NO 12
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Modified by tyrpyridine
<220> FEATURE:
<221> NAME/KEY: misc_feature
<222> LOCATION: (2)..(2)
<223> OTHER INFORMATION: n = locked nucleic acid thymine
<220> FEATURE:
<221> NAME/KEY: misc_feature
<222> LOCATION: (5)..(5)
<223> OTHER INFORMATION: n = locked nucleic acid adenine
```

```
<220> FEATURE:
<221> NAME/KEY: misc_feature
<222> LOCATION: (8)..(8)
<223> OTHER INFORMATION: n = locked nucleic acid adenine
<220> FEATURE:
<221> NAME/KEY: misc_feature
<222> LOCATION: (11)..(11)
<223> OTHER INFORMATION: n = locked nucleic acid thymine
<220> FEATURE:
<221> NAME/KEY: misc_feature
<222> LOCATION: (14)..(14)
<223> OTHER INFORMATION: n = locked nucleic acid adenine
<220> FEATURE:
<221> NAME/KEY: misc_feature
<222> LOCATION: (17)..(17)
<223> OTHER INFORMATION: n = locked nucleic acid 5-methylcytosine
<220> FEATURE:
<221> NAME/KEY: misc_feature
<222> LOCATION: (20)..(20)
<223> OTHER INFORMATION: n = locked nucleic acid 5-methylcytosine

<400> SEQUENCE: 12
gngtnacncg nctntangcn ca                                              22

<210> SEQ ID NO 13
<211> LENGTH: 51
<212> TYPE: DNA
<213> ORGANISM: Artificial Sequence
<220> FEATURE:
<223> OTHER INFORMATION: Synthetic Construct

<400> SEQUENCE: 13
aatgcactag ttcaacatca gtctgataag ctagctcagc aagcttaatg c              51

<210> SEQ ID NO 14
<211> LENGTH: 51
<212> TYPE: DNA
<213> ORGANISM: Artificial Sequence
<220> FEATURE:
<223> OTHER INFORMATION: Synthetic Construct

<400> SEQUENCE: 14
gcattaagct tgctgagcta gcttatcaga ctgatgttga actagtgcat t              51
```